United States Patent
Perkins et al.

(10) Patent No.: US 9,150,802 B2
(45) Date of Patent: Oct. 6, 2015

(54) SYSTEMS AND METHODS FOR AN INDIRECT RADIATION DRIVEN GASIFIER REACTOR AND RECEIVER CONFIGURATION

(75) Inventors: Christopher Perkins, Boulder, CO (US); Zoran Jovanovic, Louisville, CO (US); Steven Strand, Midland, MI (US); Courtland Hilton, Broomfield, CO (US); Donna Kelley, Louisville, CO (US)

(73) Assignee: Sundrop Fuels, Inc., Longmont, CO (US)

(*) Notice: Subject to any disclaimer, the term of this patent is extended or adjusted under 35 U.S.C. 154(b) by 1051 days.

(21) Appl. No.: 12/795,947

(22) Filed: Jun. 8, 2010

(65) Prior Publication Data

US 2010/0303692 A1    Dec. 2, 2010

Related U.S. Application Data

(60) Provisional application No. 61/248,282, filed on Oct. 2, 2009, provisional application No. 61/185,492, filed on Jun. 9, 2009.

(51) Int. Cl.
*C10J 3/54* (2006.01)
*C01B 3/22* (2006.01)
(Continued)

(52) U.S. Cl.
CPC ... *C10J 3/54* (2013.01); *C01B 3/22* (2013.01); *C01B 3/34* (2013.01); *C07C 29/15* (2013.01);
(Continued)

(58) Field of Classification Search
CPC .............. C10J 3/54; C10J 3/22; C10J 3/34; C10J 3/482; C10J 3/485; C10J 3/723

USPC ............................................. 48/61
See application file for complete search history.

(56) References Cited

U.S. PATENT DOCUMENTS 1,508,464 A    9/1924   McFarland
2,237,491 A    4/1941   Kutz
(Continued)

FOREIGN PATENT DOCUMENTS

JP    2002/012877 A    1/2002
SU    1763814 A1       9/1992
(Continued)

OTHER PUBLICATIONS

International Preliminary Report on Patentability for International Application No. PCT/US10/37911, dated Dec. 12, 2011, 9 pages.
(Continued)

*Primary Examiner* — Matthew Merkling
(74) *Attorney, Agent, or Firm* — Rutan & Tucker, LLP

(57) ABSTRACT

A method, apparatus, and system for a solar-driven chemical plant are disclosed. Some embodiments may include a solar thermal receiver to absorb concentrated solar energy from an array of heliostats and a solar-driven chemical reactor. This chemical reactor may have multiple reactor tubes, in which particles of biomass may be gasified in the presence of a carrier gas in a gasification reaction to produce hydrogen and carbon monoxide products. High heat transfer rates of the walls and tubes may allow the particles of biomass to achieve a high enough temperature necessary for substantial tar destruction and complete gasification of greater than 90 percent of the biomass particles into reaction products including hydrogen and carbon monoxide gas in a very short residence time between a range of 0.01 and 5 seconds.

17 Claims, 10 Drawing Sheets

(51) Int. Cl.

| | |
|---|---|
| *C01B 3/34* | (2006.01) |
| *C07C 29/15* | (2006.01) |
| *C10G 2/00* | (2006.01) |
| *C10J 3/00* | (2006.01) |
| *C10J 3/48* | (2006.01) |
| *C10J 3/72* | (2006.01) |
| *F24J 2/07* | (2006.01) |
| *C10J 3/56* | (2006.01) |

(52) U.S. Cl.
CPC ... *C10G 2/30* (2013.01); *C10J 3/00* (2013.01); *C10J 3/482* (2013.01); *C10J 3/485* (2013.01); *C10J 3/56* (2013.01); *C10J 3/723* (2013.01); *F24J 2/07* (2013.01); C01B 2203/0216 (2013.01); C01B 2203/061 (2013.01); C01B 2203/84 (2013.01); C10G 2300/1014 (2013.01); C10G 2300/1025 (2013.01); C10G 2300/807 (2013.01); C10J 2200/09 (2013.01); C10J 2300/0906 (2013.01); C10J 2300/0909 (2013.01); C10J 2300/0916 (2013.01); C10J 2300/0973 (2013.01); C10J 2300/0989 (2013.01); C10J 2300/1284 (2013.01); C10J 2300/1292 (2013.01); C10J 2300/1621 (2013.01); C10J 2300/1659 (2013.01); C10J 2300/1665 (2013.01); C10J 2300/1693 (2013.01); Y02B 40/18 (2013.01); Y02E 10/41 (2013.01); Y02E 50/18 (2013.01); Y02E 50/32 (2013.01)

(56) References Cited

U.S. PATENT DOCUMENTS

| | | | |
|---|---|---|---|
| 4,164,123 | A | 8/1979 | Smith |
| 4,219,492 | A | 8/1980 | Konoki et al. |
| 4,247,755 | A | 1/1981 | Smith, Jr. et al. |
| 4,415,339 | A | 11/1983 | Aiman et al. |
| 4,455,153 | A | 6/1984 | Jakahi |
| 4,552,741 | A | 11/1985 | Melchoir |
| 4,704,137 | A | 11/1987 | Richter |
| 4,756,722 | A | 7/1988 | Knop et al. |
| 4,766,154 | A | 8/1988 | Bonnell et al. |
| 5,179,129 | A | 1/1993 | Studer |
| 5,581,998 | A | 12/1996 | Craig |
| 5,618,500 | A | 4/1997 | Wang |
| 5,647,877 | A | 7/1997 | Epstein |
| 5,906,799 | A | 5/1999 | Burgie et al. |
| 6,660,244 | B2 | 12/2003 | Negishi et al. |
| 6,676,716 | B2 | 1/2004 | Fujimura et al. |
| 6,872,378 | B2 | 3/2005 | Weimer et al. |
| 7,033,570 | B2 | 4/2006 | Weimer et al. |
| 7,207,327 | B2 | 4/2007 | Litwin et al. |
| 7,553,476 | B2 | 6/2009 | Marrella et al. |
| 7,632,476 | B2 | 12/2009 | Shah et al. |
| 7,686,856 | B2 | 3/2010 | Hemmings et al. |
| 7,856,829 | B2 | 12/2010 | Shah et al. |
| 7,871,457 | B2 | 1/2011 | Shah et al. |
| 7,881,825 | B2 | 2/2011 | Esposito et al. |
| 7,931,888 | B2 | 4/2011 | Drnevich et al. |
| 7,985,399 | B2 | 7/2011 | Drnevich et al. |
| 8,007,761 | B2 | 8/2011 | Drnevich et al. |
| 8,378,151 | B2 | 2/2013 | Perkins et al. |
| 8,821,599 | B2 | 9/2014 | Perkins et al. |
| 2002/0134019 | A1 | 9/2002 | Paisley |
| 2003/0208959 | A1 | 11/2003 | Weimer et al. |
| 2003/0213514 | A1 | 11/2003 | Ortabasi |
| 2004/0170210 | A1 | 9/2004 | Do et al. |
| 2004/0219079 | A1 | 11/2004 | Hagen et al. |
| 2005/0020700 | A1 | 1/2005 | Bahnisch |
| 2006/0024538 | A1 | 2/2006 | Steinberg |
| 2006/0096298 | A1 | 5/2006 | Barnicki et al. |
| 2006/0140848 | A1 | 6/2006 | Weimer et al. |
| 2006/0188433 | A1 | 8/2006 | Weimer et al. |
| 2006/0225424 | A1 | 10/2006 | Elliot et al. |
| 2007/0098602 | A1 | 5/2007 | Haueter et al. |
| 2007/0129450 | A1 | 6/2007 | Barnicki et al. |
| 2007/0225382 | A1 | 9/2007 | Van Den Berg et al. |
| 2008/0057366 | A1 | 3/2008 | Katikaneni et al. |
| 2008/0086946 | A1 | 4/2008 | Weimer et al. |
| 2008/0104003 | A1 | 5/2008 | Macharia et al. |
| 2008/0209891 | A1 | 9/2008 | Johannes et al. |
| 2008/0223214 | A1 | 9/2008 | Palamara et al. |
| 2008/0284401 | A1 | 11/2008 | Oettinger et al. |
| 2008/0293132 | A1 | 11/2008 | Goldman et al. |
| 2008/0302670 | A1 | 12/2008 | Boyle |
| 2008/0307703 | A1 | 12/2008 | Dietenberger |
| 2009/0013601 | A1 | 1/2009 | Mandich et al. |
| 2009/0014689 | A1 | 1/2009 | Klepper et al. |
| 2009/0018221 | A1 | 1/2009 | Klepper et al. |
| 2009/0018222 | A1 | 1/2009 | Klepper et al. |
| 2009/0018371 | A1 | 1/2009 | Klepper et al. |
| 2009/0018372 | A1 | 1/2009 | Tirmizi et al. |
| 2009/0064578 | A1 | 3/2009 | Theegala |
| 2009/0069452 | A1 | 3/2009 | Robota |
| 2009/0069609 | A1 | 3/2009 | Kharas et al. |
| 2009/0093555 | A1 | 4/2009 | Stites et al. |
| 2009/0151251 | A1 | 6/2009 | Manzer et al. |
| 2009/0151253 | A1 | 6/2009 | Manzer et al. |
| 2009/0156392 | A1 | 6/2009 | Kharas |
| 2009/0156393 | A1 | 6/2009 | Kharas |
| 2009/0156697 | A1 | 6/2009 | Kharas |
| 2009/0313886 | A1 | 12/2009 | Hinman |
| 2009/0318573 | A1 | 12/2009 | Stites et al. |
| 2010/0000874 | A1 | 1/2010 | Hinman |
| 2010/0022806 | A1 | 1/2010 | Meitzner |
| 2010/0075837 | A1 | 3/2010 | Meitzner et al. |
| 2010/0076228 | A1 | 3/2010 | Alsum et al. |
| 2010/0099925 | A1 | 4/2010 | Kharas |
| 2010/0099926 | A1 | 4/2010 | Kharas |
| 2010/0099927 | A1 | 4/2010 | Kharas |
| 2010/0137459 | A1 | 6/2010 | Stites et al. |
| 2010/0152497 | A1 | 6/2010 | Stites |
| 2010/0152498 | A1 | 6/2010 | Kharas et al. |
| 2010/0210741 | A1 | 8/2010 | Kharas |
| 2010/0212220 | A1 | 8/2010 | Tirmizi |
| 2010/0237291 | A1 | 9/2010 | Simmons et al. |
| 2010/0242352 | A1 | 9/2010 | Perkins et al. |
| 2010/0242353 | A1 | 9/2010 | Jovanovic et al. |
| 2010/0242354 | A1 | 9/2010 | Perkins et al. |
| 2010/0243961 | A1 | 9/2010 | Hilton et al. |
| 2010/0247387 | A1 | 9/2010 | Perkins et al. |
| 2010/0249251 | A1 | 9/2010 | Hilton |
| 2010/0249468 | A1 | 9/2010 | Perkins et al. |
| 2010/0270505 | A1 | 10/2010 | Gallaspy et al. |
| 2010/0273899 | A1 | 10/2010 | Winter |
| 2010/0280287 | A1 | 11/2010 | Kharas et al. |
| 2010/0303692 | A1 | 12/2010 | Perkins et al. |
| 2010/0331581 | A1 | 12/2010 | Kharas et al. |
| 2011/0107661 | A1 | 5/2011 | Tirmizi et al. |
| 2011/0107662 | A1 | 5/2011 | Tirmizi et al. |
| 2011/0107663 | A1 | 5/2011 | Tirmizi et al. |
| 2011/0124927 | A1 | 5/2011 | Stites et al. |
| 2011/0155958 | A1 | 6/2011 | Winter et al. |
| 2011/0301732 | A1 | 12/2011 | Gao |
| 2012/0181483 | A1 | 7/2012 | Simmons et al. |
| 2012/0241677 | A1 | 9/2012 | Perkins et al. |

FOREIGN PATENT DOCUMENTS

| | | | |
|---|---|---|---|
| WO | WO 2010/144537 | A9 | 12/2010 |
| WO | WO 2010/144540 | A1 | 12/2010 |
| WO | WO 2010/144542 | A1 | 12/2010 |
| WO | WO 2010/144544 | A1 | 12/2010 |
| WO | WO 2010/144547 | A1 | 12/2010 |
| WO | WO 2010/144549 | A1 | 12/2010 |
| WO | WO 2010/144552 | A1 | 12/2010 |
| WO | WO 2010/144554 | A1 | 12/2010 |

(56) References Cited

FOREIGN PATENT DOCUMENTS

| | | |
|---|---|---|
| WO | WO 2010/144556 A1 | 12/2010 |
| WO | WO 2011/155962 A1 | 12/2011 |

OTHER PUBLICATIONS

International Preliminary Report on Patentability for International Application No. PCT/US10/37914, dated Dec. 12, 2011, 8 pages.
International Preliminary Report on Patentability for International Application No. PCT/US10/37923, dated Dec. 12, 2011, 13 pages.
International Preliminary Report on Patentability for International Application No. PCT/US10/37925, dated Dec. 12, 2011, 10 pages.
International Preliminary Report on Patentability for International Application No. PCT/US10/37930, dated Dec. 12, 2011, 13 pages.
International Preliminary Report on Patentability for International Application No. PCT/US10/37934, dated Dec. 12, 2011, 10 pages.
International Preliminary Report on Patentability for International Application No. PCT/US10/37938, dated Dec. 12, 2011, 10 pages.
International Preliminary Report on Patentability for International Application No. PCT/US10/37940, dated Dec. 12, 2011, 10 pages.
International Preliminary Report on Patentability for International Application No. PCT/US10/37944, dated Dec. 12, 2011, 10 pages.
Cross Reference to Related Applications Under 27 C.F.R. 1.78, 2 pages.
International Search Report for PCT/US10/037911, dated Aug. 6, 2010, 2 pages.
International Search Report for PCT/US10/037914, dated Aug. 13, 2010, 2 pages.
International Search Report for PCT/US10/037923, dated Aug. 9, 2010, 3 pages.
International Search Report for PCT/US10/037925, dated Aug. 10, 2010, 3 pages.
H International Search Report for PCT/US10/037930, dated Sep. 20, 2010, 5 pages.
International Search Report for PCT/US10/037934, dated Aug. 9, 2010, 2 pages.
International Search Report for PCT/US10/037938, dated Aug. 5, 2010, 2 pages.
International Search Report for PCT/US10/037940, dated Aug. 13, 2010, 2 pages.
International Search Report for PCT/US10/037944, dated Aug. 18, 2010, 2 pages.
Munzinger, M., et al., "Biomass Gass ification Using Solar Thermal Energy", *Anzses* 2006, pp. 1-10.
Mishra, Anuradha, et al., "Thermal Optimization of Solar Biomass Hybrid Cogeneration Plants", *Journal of Scientific & Industrial Research*, vol. 65, Apr. 2006, pp. 355-363.
Esser, Peter, et al., "The Photochemical Synthesis of Fine Chemicals With Sunlight," Angew. Chem. Int. Ed. Engl. 1994, vol. 33, pp. 2009-2023.
Non-Final Office Action for U.S. Appl. No. 12/796,121 mailed Jun. 7, 2012, 10 pages.
Notice of Allowance for U.S. Appl. No. 12/796,121 mailed Oct. 11, 2012, 7 pages.
Restriction Requirement Office Action for U.S. Appl. No. 12/796,428 mailed Oct. 9, 2012, 7 pages.
Written Opinion for International Application No. PCT/US2010/037923 mailed Aug. 9, 2010, 11 pages.
Restriction Requirement for U.S. Appl. No. 12/795,045 mailed Apr. 18, 2013, 5 pages. U.S. Patent and Trademark Office, Alexandria, Virginia USA.
Written Opinion for International Application No. PCT/US2010/037911 mailed Aug. 6, 2010, 7 pages.
Notice of Allowance for U.S. Appl. No. 12/796,121 mailed Oct. 11, 2012, 7 pages. U.S. Patent and Trademark Office, Alexandria, Virginia USA.
Non-Final Office Action for U.S. Appl. No. 12/796,121 mailed Jun. 7, 2012, 10 pages. U.S. Patent and Trademark Office, Alexandria, Virginia USA.
Written Opinion for International Application No. PCT/US2010/037914 mailed Aug. 13, 2010, 6 pages.
Written Opinion for International Application No. PCT/US2010/037925 mailed Aug. 10, 2010, 8 pages.
Restriction Requirement for U.S. Appl. No. 12/796,428 mailed Oct. 9, 2012, 7 pages. U.S. Patent and Trademark Office, Alexandria, Virginia USA.
Written Opinion for International Application No. PCT/US2010/037930 mailed Sep. 20, 2010, 11 pages.
Restriction Requirement for U.S. Appl. No. 12/796,471 mailed Mar. 13, 2013, 6 pages. U.S. Patent and Trademark Office, Alexandria, Virginia USA.
Written Opinion for International Application No. PCT/US2010/037934 mailed Aug. 9, 2010, 8 pages.
Non-Final Office Action for U.S. Appl. No. 12/796,471 mailed May 3, 2013, 22 pages. U.S. Patent and Trademark Office, Alexandria, Virginia USA.
Restriction Requirement for U.S. Appl. No. 12/795,910 mailed Feb. 20, 2013, 6 pages. U.S. Patent and Trademark Office, Alexandria, Virginia USA.
Non-Final Office Action for U.S. Appl. No. 12/795,947 mailed Mar. 14, 2013, 26 pages. U.S. Patent and Trademark Office, Alexandria, Virginia USA.
Restriction Requirement for U.S. Appl. No. 12/795,947 mailed Oct. 9, 2012, 5 pages. U.S. Patent and Trademark Office, Alexandria, Virginia USA.
Written Opinion for International Application No. PCT/US2010/037940 mailed Aug. 13, 2010, 8 pages.
Written Opinion for International Application No. PCT/US2010/037944 mailed Aug. 18, 2010, 8 pages.
*Netscape Communications Corp.* v. *ValueClick, Inc.*, 684 F. Supp. 2d. 678—Dist, Court, ED Virginia 2010. No. 1:09cv225. United States District Court, E.D. Virginia, Alexandria Division. Oct. 22, 2009. 38 pages.
*Ex Parte* Wada and Murphy, U.S. Patent and Trademark Office Board of Patent Appeals and Interferences Decision on Appeal dated Jan. 14, 2008, 9 pages.
*Ex Parte* Chapman, U.S. Patent and Trademark Office Board of Patent Appeals and Interferences Decision on Appeal dated Feb. 9, 2012 for Appeal No. 2009-010238, U.S. Appl. No. 10/751,616, 6 pages.
Restriction Requirement for U.S. Appl. No. 13/429,794 mailed May 24, 2013, 5 pages. U.S. Patent and Trademark Office, Alexandria, Virginia USA.
Restriction Requirement for U.S. Appl. No. 12/796,319 mailed Jun. 20, 2013, 5 pages. U.S. Patent and Trademark Office, Alexandria, Virginia USA.
Non-Final Office Action for U.S. Appl. No. 12/796,222 mailed Jan. 29, 2013, 48 pages. U.S. Patent and Trademark Office, Alexandria, Virginia USA.
Decision on Petition for the U.S. Appl. No. 12/796,045 mailed Jun. 22, 2010, 2 pages. U.S. Patent & Trademark Office, Alexandria, Virginia USA.
Notice of Allowance for U.S. Appl. No. 12/796,045 mailed Feb. 28, 2014, 13 pages. U.S. Patent and Trademark Office, Alexandria Va US.
Non-Final Office Action for U.S. Appl. No. 12/796,045 mailed Sep. 13, 2013, 7 pages. U.S. Patent and Trademark Office, Alexandria, Virginia USA.
Advisory Action for U.S. Appl. No. 12/796,471 mailed Mar. 10, 2014, 4 pages. U.S. Patent and Trademark Office, Alexandria, Virginia, USA.
Notice of Allowance for U.S. Appl. No. 12/795,910 mailed Apr. 16, 2014, 25 pages. U.S. Patent & Trademark Office, Alexandria, Virginia USA.
Office Action for Chinese Patent Application No. 201080025216.3 mailed Mar. 27, 2014, 9 pages, State Intellectual Property Office of PRC.
Decision on Petition for the U.S. Appl. No. 12/795,989 mailed Jun. 22, 2010, 2 pages. U.S. Patent & Trademark Office, Alexandria, Virginia USA.
Non-Final Office Action for U.S. Appl. No. 13/429,794 mailed Jun. 13, 2014, 20 pages. U.S. Patent and Trademark Office, Alexandria VA US.

(56) References Cited

OTHER PUBLICATIONS

Decision on Petition for the U.S. Appl. No. 12/795,910 mailed Jun. 22, 2010, 2 pages. U.S. Patent & Trademark Office, Alexandria, Virginia USA.

Final Office Action for U.S. Appl. No. 13/429,794 mailed Feb. 28, 2014, 9 pages. U.S. Patent and Trademark Office, Alexandria, Virginia USA.

Notification Concerning Transmittal of International Preliminary Report on Patentability for International Patent Application No. PCT/US2010/059564, dated Dec. 20, 2012, 10 pages. International Bureau of WIPO, Geneva, Switzerland.

Notice of Allowance for U.S. Appl. No. 12/795,910 mailed May 30, 2014, 15 pages. U.S. Patent and Trademark Office, Alexandria VA US.

International Search Report and Written Opinion for International Patent Application No. PCT/US 10/37938, dated Aug. 5, 2010, 11 pages. International Searching Authority/US Alexandria, Virginia, USA.

Final Office Action for U.S. Appl. No. 12/796,471 mailed Nov. 27, 2013, 20 pages. U.S. Patent and Trademark Office, Alexandria, Virginia, USA.

Decision on Petition for the U.S. Appl. No. 12/796,471 mailed Jun. 22, 2010, 2 pages. U.S. Patent & Trademark Office, Alexandria, Virginia USA.

Non-Final Office Action for U.S. Appl. No. 12/795,910 mailed Sep. 12, 2013, 7 pages. U.S. Patent & Trademark Office, Alexandria, Virginia USA.

Office Action for Chinese Patent Application No. 201080025216.3 mailed Jun. 20, 2013, 7 pages, State Intellectual Property Office of PRC.

Notification of Transmittal of the International Search Report and the Written Opinion of the International Searching Authority for International Application No. PCT/US10/059564 mailed Mar. 2, 2011, 11 pages. International Searching Authority/US, Alexandria, Virginia USA.

Non-Final Office Action for U.S. Appl. No. 13/429,794 mailed Nov. 1, 2013, 7 pages. U.S. Patent and Trademark Office, Alexandria, Virginia, USA.

Non-Final Office Action for U.S. Appl. No. 12/796,471 mailed May 3, 2013, 19 pages. U.S. Patent and Trademark Office, Alexandria, Virginia USA.

Final Office Action for U.S. Appl. No. 12/795,989 mailed Jul. 16, 2013, 28 pages. U.S. Patent and Trademark Office, Alexandria, Virginia USA.

Non-Final Office Action for U.S. Appl. No. 12/795,989 mailed Jan. 24, 2013, 29 pages. U.S. Patent and Trademark Office, Alexandria, Virginia USA.

Decision on Petition for the U.S. Appl. No. 12/796,121 mailed Jun. 22, 2010, 2 pages. U.S. Patent & Trademark Office, Alexandria, Virginia USA.

Non-Final Office Action for U.S. Appl. No. 12/796,471 mailed Jun. 25, 2014, 23 pages. U.S. Patent and Trademark Office, Alexandria VA US.

Notice of Allowance for U.S. Appl. No. 13/254,020 mailed Dec. 3, 2014 7 pages. U.S. Patent and Trademark Office, Alexandria, Virginia USA.

Advisory Action for U.S. Appl. No. 13/429,794 mailed Feb. 3, 2015 3 pages. U.S. Patent and Trademark Office, Alexandria, Virginia USA.

Final Office Action for U.S. Appl. No. 13/429,794 mailed Oct. 15, 2014 21 pages. U.S. Patent and Trademark Office, Alexandria, Virginia USA.

Final Office Action for U.S. Appl. No. 12/796,222 mailed Jan. 21, 2015 6 pages. U.S. Patent and Trademark Office, Alexandria, Virginia USA.

Final Office Action for U.S. Appl. No. 12/796,471 mailed Nov. 12, 2014 28 pages. U.S. Patent and Trademark Office, Alexandria, Virginia USA.

SYSTEMS AND METHODS FOR AN INDIRECT RADIATION DRIVEN GASIFIER REACTOR AND RECEIVER CONFIGURATION

RELATED APPLICATIONS

This application claims the benefit of both U.S. Provisional Patent Application Ser. No. 61/248,282, filed Oct. 2, 2009 and entitled "Various Methods and Apparatuses for Sun Driven Processes," and U.S. Provisional Patent Application Ser. No. 61/185,492, titled "VARIOUS METHODS AND APPARATUSES FOR SOLAR-THERMAL GASIFICATION OF BIOMASS TO PRODUCE SYNTHESIS GAS" filed Jun. 9, 2009.

NOTICE OF COPYRIGHT

A portion of the disclosure of this patent document contains material that is subject to copyright protection. The copyright owner has no objection to the facsimile reproduction by anyone of the software engine and its modules, as it appears in the Patent and Trademark Office Patent file or records, but otherwise reserves all copyright rights whatsoever.

FIELD OF THE INVENTION

Embodiments of the invention generally relate to systems, methods, and apparatus for refining biomass and other materials. More particularly, an aspect of an embodiment of the invention relates to solar-driven systems, methods, and apparatus for refining biomass and other materials.

BACKGROUND OF THE INVENTION

Biomass gasification is an endothermic process; energy must be put into the process to drive it forward. Typically, this is performed by partially oxidizing (burning) the biomass itself. Between 30% and 40% of the biomass must be consumed to drive the process, and at the temperatures which the process is generally limited to (for efficiency reasons), conversion is typically limited, giving still lower yields. In contrast, the proposed solar-driven biorefinery uses an external source of energy (solar) to provide the energy required for reaction, so none of the biomass need be consumed to achieve the conversion. This results in significantly higher yields of gasoline per biomass ton than previous technologies. As the energy source being used to drive the conversion is renewable and carbon free. Also, chemical reactors are generally engineered to operate at constant conditions around the clock.

SUMMARY OF THE INVENTION

Some embodiments relate to a solar-driven chemical plant that may include a solar thermal receiver to absorb concentrated solar energy from an array of heliostats. Some embodiments can include a solar-driven chemical reactor. This chemical reactor may have multiple reactor tubes located inside the solar thermal receiver. In the multiple reactor tubes, particles of biomass may be gasified in the presence of a carrier gas in a gasification reaction to produce hydrogen and carbon monoxide products. These products can have an exit temperature from the tubes exceeding 900 degrees C. Additionally, the multiple reactor tubes in the reactor design may increase available reactor surface area for radiative exchange to the biomass particles as well as inter-tube radiation exchange.

Additionally, in some embodiments, one or more apertures 1) open to an atmosphere of the Earth or 2) covered by a window may be used to pass the concentrated solar energy into the solar thermal receiver. This energy may impinge on the multiple reactor tubes and cavity walls of the receiver, wherein the reactor tubes serve the dual functions of 1) segregating the biomass gasification reaction environment from the atmosphere of the Earth and 2) transferring energy by solar radiation absorption and heat radiation, convection, and conduction. This can drive the reacting particles in an endothermic gasification reaction of the particles of biomass flowing through the reactor tubes. Additionally, high heat transfer rates of the walls and tubes may allow the particles of biomass to achieve a high enough temperature necessary for substantial tar destruction and complete gasification of greater than 90 percent of the biomass particles into reaction products including hydrogen and carbon monoxide gas in a very short residence time between a range of 0.01 and 5 seconds.

An inner wall of the cavity, wherein the inner wall and the reactor tubes exchange energy primarily by radiation, not by convection or conduction may allow for the reactor tubes to achieve a fairly uniform temperature profile even though the concentrated solar energy is merely directly impinging on the reactor tubes from one direction. Additionally, the radiation heat transfer from the inner wall and the reactor tubes may be the primary source of energy driving the gasification reaction in which the small biomass particles act as millions of tiny absorbing surfaces of radiant heat energy coming from the inner wall and the tubes.

An on-site chemical or fuel synthesis reactor that is geographically located on the same site as the chemical reactor and integrated to receive the hydrogen and carbon monoxide products from the gasification reaction may also be used. The on-site chemical or fuel synthesis reactor may be configured to use the hydrogen and carbon monoxide products in a hydrocarbon fuel synthesis process to create a liquid hydrocarbon fuel.

BRIEF DESCRIPTION OF THE DRAWINGS

The drawings refer to embodiments of the invention in which.

Figure 1:
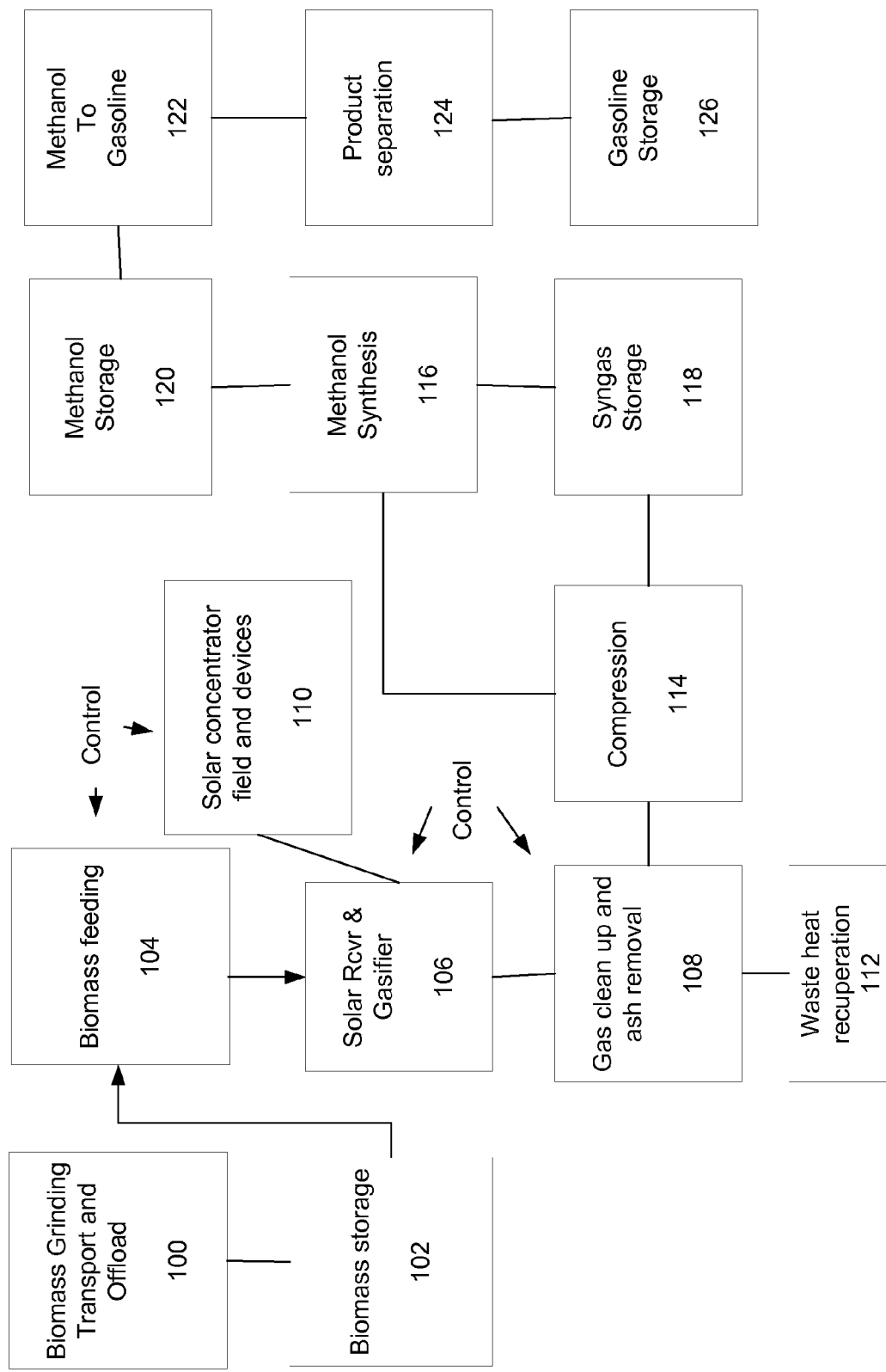
FIG. 1 illustrates a block diagram of an embodiment of an example process flow.

While the invention is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the invention.

DETAILED DISCUSSION

In the following description, numerous specific details are set forth, such as examples of specific data signals, named components, connections, number of reactor tubes, etc., in order to provide a thorough understanding of the present invention. It will be apparent, however, to one of ordinary skill in the art that the present invention may be practiced without these specific details. In other instances, well known components or methods have not been described in detail but rather in a block diagram in order to avoid unnecessarily obscuring the present invention. Further specific numeric references such as first reactor tube, may be made. However, the specific numeric reference should not be interpreted as a literal sequential order but rather interpreted that the first reactor tube is different than a second reactor tube. Thus, the specific details set forth are merely exemplary. The specific details may be varied from and still be contemplated to be within the spirit and scope of the present invention. The term coupled is defined as meaning connected either directly to the component or indirectly to the component through another component.

In general, the solar-driven chemical plant includes a biomass feed system. The system may be feedstock flexible because the gasification energy is external to the biomass itself. The biomass is not combusted, and a combustion reaction does not need to be managed at the same time as the gasification reaction; thus, eliminating the need for a specialized reactor geometry for each type of biomass. One example system includes a chemical reactor and an on-site fuel synthesis reactor. The chemical reactor may receive concentrated solar thermal energy from an array of heliostats and this energy can be used to refine the biomass. A heliostat is generally a device that tracks the movement of the sun and typically utilizes a mirror to redirect sunlight toward a stationary target or receiver such as a solar thermal tower.

Some embodiments of a solar-driven chemical plant can include a material making up the inner wall of the receiver cavity that has mechanical and chemical properties to retain its structural strength at high temperatures (between 1100-1500° C.). Additionally, the material may have very high emissivity ($\epsilon$>0.9) or high reflectivity ($\epsilon$<20%) as well as high heat capacity and low thermal conductivity for the receiver cavity. Where the very high emissivity of $\epsilon$>0.9 is the ratio of the radiant energy emitted by a surface to that emitted by a blackbody at the same temperature, and the high reflectivity of $\epsilon$>90% is the percentage of incident radiation reflected by a surface. The material of the reactor tubes can also possess high emissivity, high thermal conductivity, and moderate to high heat capacity. In some examples, the tube material is resistant to the oxidizing air environment in the cavity and the reducing environment of the biomass gasification reaction. The rapid exchange of heat between the reactor tubes and the biomass particles allows for the rapid gasification of the dispersed falling biomass particulates with a resultant stable ash formation and amelioration of tar to less than 500 milligrams per normal cubic meter millimeter. In some embodiment, amelioration of tar is less than 50 milligrams per normal cubic meter millimeter. Additionally, such a system may provide for the production of the hydrogen and carbon monoxide products. In some embodiments, an inner wall of the receiver cavity may be made of a solar energy-absorbing material rather than a highly reflective material.

At high temperatures, the cavity walls and the tube surfaces exchange energy due to thermal radiation. The tube surface area may be configured to increase directly proportional to the fourth power of an absolute temperature of the cavity walls and tubes surfaces.

In some embodiments, a high solar energy flux from the heliostat field to give equal to or greater than three MW per meters squared of solar energy at the apertures. This may give the receiver cavity to have a capacity of at least 2000 kW and generally around 80,000 kW. Additionally, multiple reactor tubes within the cavity may increase the surface area for radiative transfer to the biomass particles.

FIG. 1 illustrates a block diagram of an embodiment of an example process flow. Some embodiments encompass a solar-driven-biomass gasification to liquid fuel/electrical process. The process might also include electrical generation, chemical processing, or bio-char, for solar generated syngas derivative product or other similar technical process. In a specific example implementation the process described is a solar-driven-biomass gasification to 'green' liquid fuel process. In an embodiment, this process includes one or more of the following process steps.

Biomass grinding or densification, transport and offload 100 may be part of the overall process. Bales of biomass can be double compressed by a compactor to facilitate transport on-site via the densification achieved by the double compression and the bales are sized to dimensions that may, for example, fit within a standard box car size or fit within standard compactor size. The entrained-flow biomass feed system can be preceded by a grinding system equipped with mechanical cutting device and a particle classifier, such as a perforated screen or a cyclone, to control the size of the particles that are fed to the feed system. The grinding system that has a mechanical cutting device such as a screw and set of filters with micron sized holes/screen diameter sized holes to control particle size. The biomass may be in an embodiment non-food stock biomass. In some cases, food stock biomass might also be processed.

The biomass may then be stored 102. As needed, the biomass might be fed 104 into an example system or apparatus of the instant application. For example, after grinding and pulverizing the biomass to particles, the particles of biomass can be fed into and gasified in the solar-driven chemical reactor. Two or more feed line supply the particles of biomass having an average smallest dimension size between 50 microns (um) and 2000 um.

A solar receiver and gasifier 106 may be used to break down the biomass. An example biomass gasifier design and operation can include a solar chemical reactor and solar receiver to generate components of syngas. An indirect radiation driven geometry of the solar receiver and gasifier 106, in the form of an absorbing, integrating cavity, drives chemical reactions. An inner wall of the receiver cavity and the reactor tubes exchange energy primarily by radiation, not by convection or conduction, allowing for the reactor tubes to achieve a fairly uniform temperature profile even though the concentrated solar energy is only directly impinging on the reactor tubes from a limited set of angles predicted by the geometric arrangement of the heliostat field. The radiation heat transfer from the inner wall and the reactor tubes is the primary source of energy driving the gasification reaction. High heat transfer rates of the reactor tubes and cavity walls of the receiver allow the particles of biomass to achieve a high enough temperature necessary for substantial tar destruction and complete gasification of greater than 90 percent of the biomass particles into reaction products including the hydrogen and carbon monoxide gas in a very short residence time between a range of 0.01 and 5 seconds. Various heliostat field designs and operations provide the focused beam of concentrated energy may be used. Some example systems may include a solar concentrator, secondary concentrator, focused mirror array, etc. to drive biomass gasifier 110.

Quenching, gas clean up, and ash removal from biomass gasifier 108 may be provided for. Some purge syngas may exit the system 112, especially during plant startup and shutdown. Some gasses may be a waste product, while other gasses can be compressed 114 prior to storage 118 or e.g., methanol synthesis 116. Methanol may then be stored 120 for later methanol to gasoline conversion 122.

Some embodiments can include an on-site chemical synthesis reactor, such as a fuel synthesis reactor, that is geographically located on the same site as the chemical reactor and integrated to receive the hydrogen and carbon monoxide products from the gasification reaction. The on-site chemical synthesis reactor is configured to use the hydrogen and carbon monoxide products for a hydrocarbon synthesis process performed in the on-site chemical synthesis reactor to create hydrocarbon fuels and/or chemicals.

In various embodiments, synthesis gas may be a feedstock to another technical application. Examples include a syngas to other chemical conversion process. The other chemical of chemicals produced can include liquefied fuels such as transportation liquefied fuels. In an example, hydrocarbon based fuel Methanol 116 may be formed from syngas. The methanol may be further converted to gasoline or other fuels 122 and various products may be separated out from the gasoline 124 or syngas. These products, e.g., gasoline, may then be stored for later use as an energy source.

Some embodiments of the systems and methods described herein can include a controller, such as a computerized controller. The tuning and predictive parameters for this controller may be optimized for the full-scale receiver/reactor system, where lag times and dynamic response parameters of various process variables, including heliostat response time, biomass feed variability and response time, etc., are taken into account. Control system tuning may be adaptive, adjusting to parameters at peak, mid, and trough solar energy conditions.

Figure 2:
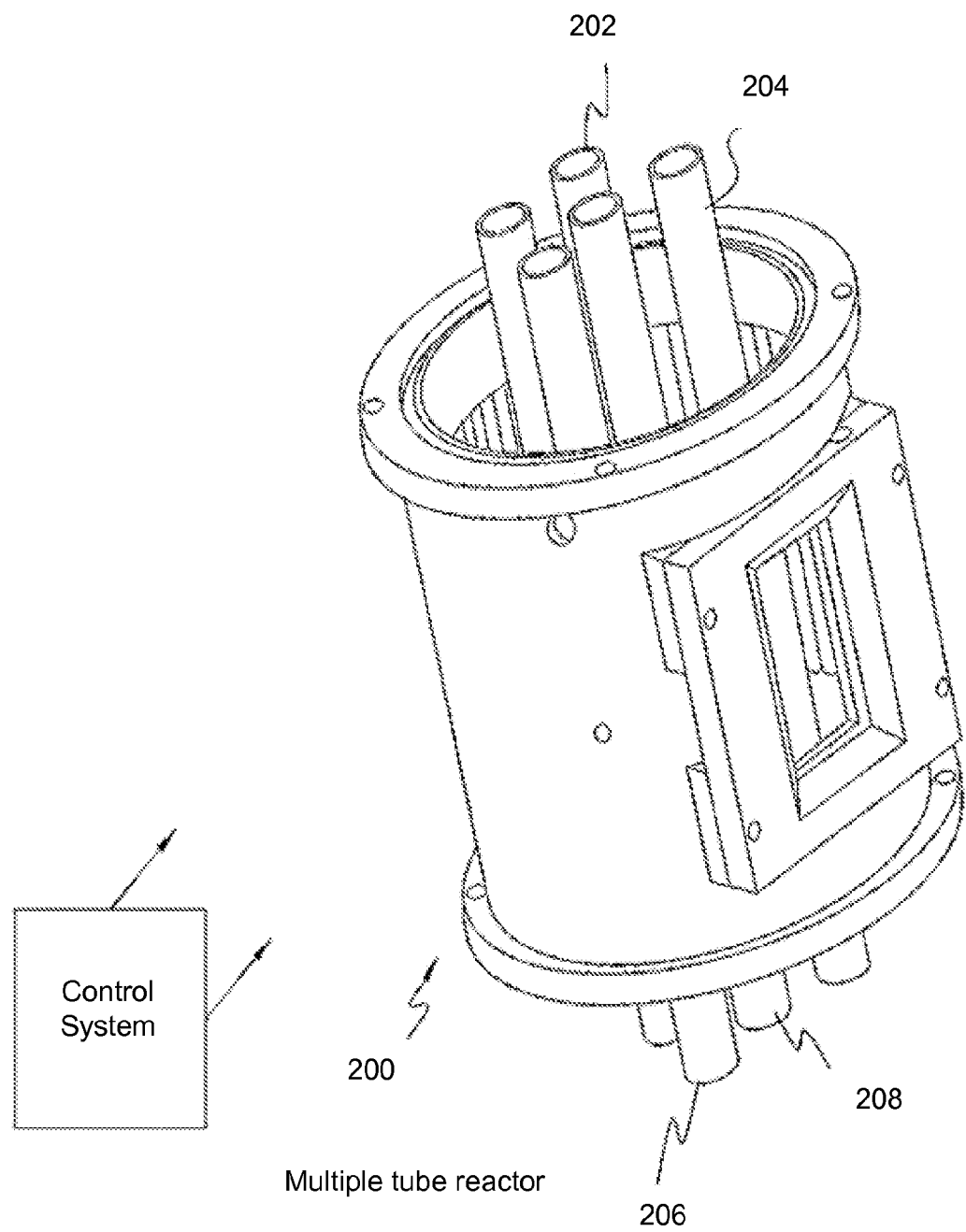
FIG. 2 illustrates a diagram of an embodiment of an example multiple tube reactor.

FIG. 2 illustrates a diagram of an example multiple tube chemical reactor 200 that may be used in a solar-driven system. Reactor 200 has multiple reactor tubes 202, 204, 206, 208 and a separate entrainment line may be used for each of the gasifier reactor tubes 202, 204, 206, 208 in the chemical reactor 200. This may allow for independent temperature control and balancing of amount of particles of biomass flowing in each of the reactor tubes 202, 204, 206, 208 in the multiple tube solar-driven chemical reactor 200. The particles of biomass feed can be distributed to the reactor tubes 202, 204, 206, 208 by a lock hopper rotary feed system, such as a Rotofeed® lock hopper rotary feed system. The lock hopper rotary feed system controls, for example, the rotational rate of the screw or auger that can move set amounts of biomass along the axis of rotation of the auger. Such a system can allow for balanced feeding to individual reactor tubes 202, 204, 206, 208 and feed rate of the particles is controlled by a weight measuring metering device such as load cells.

A solar-driven chemical plant can include a solar thermal receiver having a cavity with an inner wall. The solar thermal receiver is aligned to absorb concentrated solar energy from one or more of 1) an array of heliostats, 2) solar concentrating dishes, and 3) any combination of the two. A solar-driven chemical reactor may have multiple reactor tubes at least partially or fully located inside the cavity of solar thermal receiver. The receiver is the cavity that collects and distributes the solar energy, while the reactor tubes are the individual transport tubes in which the gasification reaction takes place.

Various embodiments can include a biomass gasifier reactor 200 and receiver configuration that can include various reactor dimensions, shape, and material. For example, a solar-driven chemical reactor 200 that has multiple reactor tubes 202, 204, 206, 208 in a downdraft geometry may be used. The multiple reactor tubes 202, 204, 206, 208 can be located inside the solar thermal receiver. In the multiple reactor tubes 202, 204, 206, 208 particles of biomass may be gasified in the presence of a carrier gas in an endothermic gasification reaction to produce hydrogen and carbon monoxide products at an exit gas temperature from the tubes that equals or exceeds 900 degrees C.

In some embodiments, one or more apertures in the receiver 1) open to an atmosphere of the Earth or 2) with a window covering the aperture, used to pass concentrated solar energy into the solar thermal receiver to impinge on the multiple reactor tubes 202, 204, 206, 208 and cavity walls of the receiver. The reactor tubes 202, 204, 206, 208 serve the dual functions of 1) segregating the biomass gasification reaction environment from the atmosphere of the Earth and 2) transferring energy by solar radiation absorption and heat radiation, convection, and conduction. This energy is transferred to the reacting particles to drive the endothermic gasification reaction of the particles of biomass flowing through the reactor tubes 202, 204, 206, 208. High heat transfer rates of the materials making up the cavity walls and the reactor tubes 202, 204, 206, 208 allows the particles of biomass to achieve a high enough temperature necessary for substantial tar destruction and complete gasification of greater than 90 percent of the particles into reaction products including hydrogen and carbon monoxide gas in a very short residence time between a range of 0.01 and 5 seconds.

The multiple reactor tubes 202, 204, 206, 208 are oriented vertically in the solar receiver cavity. The biomass particles are introduced at the top of the reactor tubes 202, 204, 206, 208, entrained by the carrier gas such as steam, and are directed by gravity and pressure through a gasification reaction zone of the reactor tubes 202, 204, 206, 208. Temperatures of operation can be clearly delineated with the receiver cavity wall temperatures between 1100 degrees C. and 1450 degrees C. and a gas temperature from an exit of the gasification reaction zone of the reactor tubes 202, 204, 206, 208 is in excess of 900 degrees C. A maximum temperature may be set somewhere below the silica melting temperature.

In some embodiments, the solar-driven chemical plant includes reactor tubes 202, 204, 206, 208 with an inner diameter and solids holdup to allow a substantially uniform gasification of biomass particles from the edges to the center of the tube. Some have a wall thickness set to withstand at least a 75 psig pressure at 1400° C. on the inside tube walls.

Note, a chemical reactor is the container in which a chemical reaction occurs. Also, the chemical reactor may be a single reactor tube, or a set of reactor tubes. Thus, the chemical reactor may be a single reactor with multiple reactor tubes or multiple reactors each being a single reactor tube, or some other similar combination. Further, different chemical reactions may take place in different reactor tubes of the solar-driven chemical reactor. For example, Steam Methane Reforming may occur in a first set of reactor tubes and biomass gasification may occur in another set of reactor tubes making up the chemical reactor, which is at least partially contained in the solar thermal receiver. Also, the control system may control the chemical reactions occurring within the reactor tubes via a number mechanisms as described herein.

For example, the flow rate of the chemical reactants, such as biomass particles and carrier gas, into and through the reactor tubes is controlled, along with a concentration of each reactant flowing through the reactor tube. The control system may control each reactor tube individually, or in sets/groups of for example clusters of eighteen tubes, or all of the tubes in their entirety. The shape, orientation, and other features of the reactor tubes may vary as described herein. Note, for contrast purposes, more than one chemical reactor may be located on a common tower such as in FIG. 3. The example shows a first chemical reactor, a second chemical reactor, and a third chemical reactor contained at least partially within its own associated solar thermal receiver. The first, second, and third chemical reactors located on the same tower may not share a common control system or a common solar thermal receiver, and thus, are truly each distinct chemical reactors. However, they all may be fed from some common feed vessels/lock hoppers and/or may share downstream quenching and gas clean up system components.

The one or more apertures may be part of a receiver outer shell that at least partially encloses multiple reactor tubes 202, 204, 206, 208. The receiver shell may absorb or highly reflect the concentrated solar energy, either heating the shell and re-radiating the energy or reflecting the radiation to convey the radiant energy to the reactor tubes of the solar-driven chemical reactor 200. Additionally, an inner wall of the receiver cavity may be made of material to allow the receiver cavity to be operated at high (>1200° C.) wall temperatures. This can enable high reactor tube temperatures, thus enabling high heat transfer rates, rapid reaction kinetics, and high selectivity to syngas.

Some embodiments of the solar-driven chemical plant described herein include an opaque wall for each of the reactor tubes 202, 204, 206, 208. In such a system an inner wall of the receiver and the reactor tubes 202, 204, 206, 208 may exchange energy primarily by radiation. This can allow for the reactor tubes 202, 204, 206, 208 to achieve a fairly uniform temperature profile even though the concentrated solar energy from the heliostats and/or solar concentrating dishes is only directly impinging on the reactor tubes 202, 204, 206, 208 from one direction. The radiation heat transfer from the inner wall and the reactor tubes 202, 204, 206, 208 may be the primary source of energy driving the gasification reaction in which the small biomass particles to act as millions of tiny absorbing surfaces of radiant heat energy coming from the inner wall of the tubes.

Because of the high temperatures in the receiver cavity, the materials used to make up a wall of the receiver cavity may have mechanical and chemical properties to maintain their strength at high temperatures (between 1100° C.-1500° C.). For the receiver cavity, these materials can have very high emissivity or high reflectivity as well as high heat capacity and low thermal conductivity. Additionally, the material of the reactor tubes 202, 204, 206, 208 may possess high emissivity, high thermal conductivity, and moderate to high heat capacity. Further, the material can be resistant to both the oxidizing air environment in the cavity as well as the reducing environment on the tube interior. The high reaction temperatures result in amelioration of tar to less than 50 milligrams per normal cubic meter, and the production of the hydrogen and carbon monoxide products.

Figure 9:
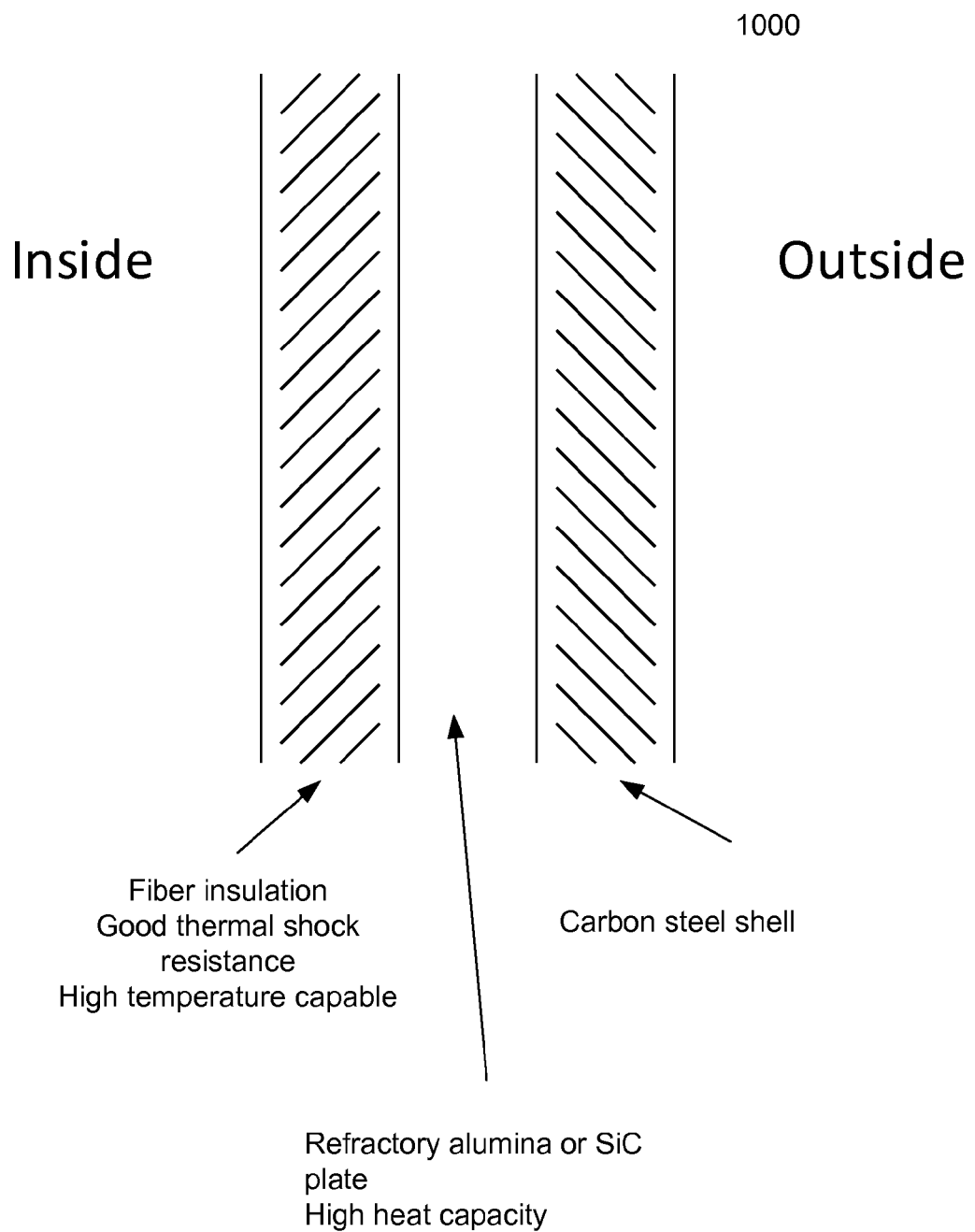
FIG. 9 illustrates a diagram of an embodiment of the walls of the solar thermal receiver.

FIG. 9 illustrates a diagram of an embodiment of the walls of the solar thermal receiver 900. In some embodiments, the inside walls of the receiver cavity are lined with alumina (or similar material) fiber insulation, with a thickness of 24 cm, for example, to provide good resistance to thermal shock. Outside of this fiber insulation layer can be refractory alumina or SiC plate. The receiver may be contained by a structural carbon steel shell with a thickness of, for example, 0.125" wall thickness, where there is an air gap with a thickness of, for example, 2", beyond this carbon steel shell. This air gap is to prevent thermal losses. A second carbon steel shell of the same thickness as before may be used. This second carbon steel shell may further contain the conductive losses from the cavity. The wall thickness of the insulation may be designed so as to limit losses to less than 5% of the energy incident on the aperture or window of the solar thermal receiver.

In some embodiments, the solar-driven chemical plant may include first and second reactor tubes of the multiple tubes 202, 204, 206, 208. The tubes 202, 204, 206, 208 can be materially made of refractory ceramics or metals. The material chosen must have good chemical stability and high strength at high temperatures (1100° C.-1500° C.). Additionally, material with high corrosion and abrasion resistance to the biomass (particle size, type, inorganic content), high corrosion resistance to the steam concentration and good resistance to brittleness from solar flux may be selected. Good thermal shock resistance may provide protection from rapid changes in available solar energy.

In some embodiments, the material used for the reaction tubes may have high oxidation resistance at high temperatures if the receiver cavity is filled with a non-inert gas such as air. Some embodiments include material good at absorbing solar energy, high re-radiating properties via radiation emissivity, and high thermal conductivity. Oxidation resistance can be provided by a coating of silicon carbide between 0.001" and 0.020" thick. This coating may be placed on the reactor tube through chemical vapor deposition or through direct siliconization of the graphite and the reactor tubes 202, 204, 206, 208.

In some examples, the solar-driven chemical plant may have length and diameter dimensions of a gasification reaction zone of each of the reactor tubes 202, 204, 206, 208 that may be sized to give a fast residence time of 0.01 second to 5 seconds at the gasification temperatures. The multiple tubes may have different diameters. Thus, a first tube may have a different diameter than a second tube of the multiple tubes making up the chemical reactor. Additionally, the shape of each tube might be a cylindrical shaped pipe or a rectangular shaped pipe.

In some embodiments, a solar-driven chemical plant may include a downdraft geometry to the multiple reactor tubes 202, 204, 206, 208 in which the biomass particles fall through the downdraft reactor design. The downdraft carries volatile alkali, ash, and any tars present along with the hydrogen and carbon dioxide products to the cooling zone. There is no chance of disengagement of the alkali glass as there is in an updraft or fluidized bed. The alkalis cool and nucleate on the ash. A radiation heat transfer of the cavity walls and tubes surfaces may be configured to increase with a fourth power of temperature of the surfaces. The radiation heat transfer from the material selected and shape of the cavity walls and tubes surfaces generates the temperature of greater than the 900 degrees C. with high heat transfer rates that allow the biomass particles to achieve the high temperatures necessary for tar destruction and complete gasification in the very short residence times of 0.01 seconds to 5 seconds.

For example, the biomass particles may fall through the downdraft reactor to substantially eliminate an undesirable build-up of product on the tube walls in the reaction zone that could lead to reduced heat transfer and even clogging of the tube because of the pressure and gravity pulling the particles through the reaction zone of the reactor tube. Additionally, low surface area to volume ratios may give less surface area for the material to stick on.

In some embodiments, the solar-driven chemical plant may include two or more feed lines in the multiple reactor tubes 202, 204, 206, 208. Each feed line may supply a reactor tube, wherein each feed line controls a dispersion pattern of the biomass particles into its corresponding reactor tube. This may be done to maximize radiation absorption by the particles when injected into the reactor tube based on a shape and width of the outlet of the feed line pipe carrying the biomass particles to its corresponding reactor tube.

The indirect radiation driven geometry in the form of the cavity wall of the solar thermal receiver integrates with the solar-driven chemical reactor by at least partially and possibly fully surrounding the tubes 202, 204, 206, 208 of the reactor. The receiver may be configured with only one or, in some examples, more apertures and no windows. The cavity of the receiver can also have a high concentration of solar energy at the one or more apertures. Additionally, multiple reactor tubes 202, 204, 206, 208 may be located in the center of the cavity.

Various embodiments include an insulation layer around the cavity of the solar thermal receiver, absorbing cavity, and solar thermal receiver. The thickness of the insulation can be set to control conductive heat losses from the cavity. The heliostats are aligned with the one or more apertures in the cavity to have a high average concentration of solar energy greater than 1000 suns at the one or more apertures. A shape of the cavity is designed so an average temperature in the cavity and the average concentration of solar energy at the one or more apertures control radiative losses from the cavity. Note that losses are generally controlled by the concentration of solar energy at all of the apertures.

In some embodiments, a design and orientation of the aperture, and cavity working fluid (buoyancy) are set to control convective losses. The inner cavity wall at least partially encloses the multiple reactor tubes 202, 204, 206, 208 to act like an oven, spreading heat flux around through radiation and giving a much more even temperature profile on the reactor tubes, both azimuthally and axially, than the incident solar radiation by itself would generate. Additionally, an averaging effect on the temperature radiated from the absorbing cavity walls and multiple tubes occurs within the cavity.

The concentrated solar energy from the heliostat field may impinge on the axis of the reactor tubes 202, 204, 206, 208 themselves through the course of each day. Additionally, 1) the oven effect of the cavity along with 2) the particles of biomass, which tend to average energy amongst themselves at their design volumetric loadings, combine to give the fairly uniform temperature profile and subsequent fairly uniform radial reaction profile of the biomass particles.

Additionally, the indirect radiation driven cavity reactor may have an aperture and no window. In such a system, there is no need for a window (so no need to cool or keep such a window clean) and the reaction environment is sealed off from the cavity environment by the reactor tubes. While there is some efficiency loss for not directly irradiating the reacting solids, at high temperature radiation heat transfer makes the required temperature difference very low (as it increases as temperature to the fourth power). The efficiency gains in not needing a window and rapid entrained flow kinetics far outweigh the indirect radiation losses. The solar energy from the array of heliostats may be directed onto tubes and in the reactor cavity where that energy is required.

In some examples of the systems and methods described herein, the solar-driven chemical plant can include length and diameter dimensions of a gasification reaction zone of each of the reactor tubes 202, 204, 206, 208, along with an arrangement and an amount of the tubes that may be matched to an amount of sun concentration from the heliostat field. This can give the fast residence time of 0.01 second to 5 seconds at the gasification temperatures. For example, a first of the multiple tubes may have a different diameter than a second of the multiple tubes. Tubes in the higher solar concentrations and higher in the cavity, i.e. higher oven temperature zone, may be bigger in diameter, and the bigger diameter tubes may be located in other areas of the receiver. Additionally, the shape of each tube might be a cylindrical shaped pipe, a rectangular shaped pipe, or some other shaped pipe. Additionally, in an embodiment, one or more apertures and no windows exist in the shell of the cavity. The gasification reaction zone in the multiple tubes has an inner atmosphere of the tubes, which is sealed from and not tolerant to oxygen from an environment present in the cavity.

Some embodiments may include a substantial axial length of the reactor tube for the biomass particles to be passed through the reaction zone of the reactor tube along a predetermined path. This path can be substantially coincident with the reactor tube axis. Additionally, the biomass particle reactants may be confined entirely within the reactor tube. In some examples, an arrangement of the cavity may cause high intensity radiant energy from the walls and tubes to be directed through the reactor tubes 202, 204, 206, 208 to coincide with the reaction zone of each reactor tube, either by absorption, conduction, and re-radiation (opaque tubes) or by transmission (transparent tubes).

Sufficient radiant energy may be absorbed in the reaction zone of the reactor tube to raise the temperature of the reactants to a level required to initiate and sustain the desired chemical reaction of the organic compound. Turbulent flow and/or possible buoyancy driven recirculation, both of which can happen in different operational regimes in the reactor tubes 202, 204, 206, 208 may be used. Additionally, turbulent flow has an average path that follows the axis of a reactor tube.

Various embodiments of a solar-driven chemical plant may include one or more windows and no apertures in a shell of the receiver. The window is constructed of material at least partially transparent to visible radiation but reflecting to infrared radiation, which allows the re-radiation from the hot cavity to be trapped and redirected to the reactor tubes 202, 204, 206, 208, improving overall efficiency. Additionally, the window may be constructed of one or more of the following materials quartz, sapphire, tiled sheets of sapphire, or another suitable material and coated with any number of anti-reflective and reflective coatings to achieve the desired suite of reflective and transmissive properties. For example sapphire may be used as a material for the windows that enable the use of graphite material for multiple tubes, wherein the sapphire window may allow the receiver to be enclosed and the volume in the receiver cavity is flooded with an inert gas (e.g. N2 or Ar), excluding O2 from the graphite tubes.

In some embodiments, the solar-driven chemical plant may use a material for multiple tubes that includes semi transparent sapphire, SiC coated graphite, Si/SiC composites, mullite, and ceramic matrix composites (melt infiltrated SiC/SiC). The multiple tubes have added 1) abrasion resistant coating, 2) heat resistant coating to withstand temperatures >1000 degrees C., and/or 3) corrosion resistant coating, and wherein the coatings may be added onto the reactor tubes and receiver cavity inner surfaces in a number of ways such as sputtering, chemical vapor deposition, atomic layer deposition, or physical vapor deposition, etc.

A solar-driven chemical plant may also include a chamber of the solar thermal receiver that contains additional structures to the reactor tubes 202, 204, 206, 208, which have high temperature storage material that absorb the concentrated solar energy and use one or more radiant heat masses to keep the reactor tubes 202, 204, 206, 208 hot during long periods of off sun, during cyclic up and down times in the plant, as well as keep radiant temperature in the reactor 200 more stable during normal operation.

In various embodiments a solar-driven chemical plant may include an outer shell of a receiver that has one or more windows. In such an embodiment, an array of heliostats can focus concentrated solar energy thru the windows. Additionally, at least one of the windows may include a French window design with an air/gas curtain design having positive pressure blower or negative pressure vacuum.

A solar-driven chemical plant may include a hood made of metal or ceramic that overhangs an aperture of the receiver cavity to disrupt convective currents into and out of the receiver. The receiver is the shell around the reactor tubes 202, 204, 206, 208, which the receiver absorbs or highly reflects solar flux to cause the radiant heat and then generally radiatively conveys that heat to the particles in the tubes of the reactor 200. Additionally, an aperture in the receiver cavity may be covered in very thin mesh made of transparent high temperature plastic or high heat resistance steel material to keep undesirable objects from entering the cavity from the environment.

The solar-driven chemical plant may be configured such that sufficient radiant energy is absorbed in the reaction zone of the reactor tube to raise the temperature of the reactants to a level required to initiate and sustain the desired chemical reaction of the organic compound.

Some embodiments include a solar thermal receiver to absorb concentrated solar energy from one or more of 1) an array of heliostats, 2) solar concentrating dishes, and 3) any combination of the two. A solar-driven chemical reactor 200 may include multiple reactor tubes 202, 204, 206, 208 in a downdraft geometry located inside the solar thermal receiver. The multiple reactor tubes 202, 204, 206, 208 may provide a chamber for a chemical reaction driven by radiant heat occurs. Additionally, the multiple reactor tubes 202, 204, 206, 208 in this solar-driven chemical reactor design increase available reactor surface area for radiative exchange to the reactants and inter-tube radiation exchange. The chemical reaction may include one of biomass gasification, steam methane reforming, methane cracking, steam methane cracking to produce ethylene, metals refining, and CO2 or H2O splitting to be conducted in this chemical reactor 200 using solar thermal energy from the absorbed concentrated solar energy.

Some embodiments include an aperture open to an atmosphere of the Earth or with a window, to pass the concentrated solar energy into the solar thermal receiver to impinge on the multiple reactor tubes 202, 204, 206, 208 and cavity walls of the receiver. The reactor tubes 202, 204, 206, 208 serve the dual functions of 1) segregating the chemical reaction environment from the atmosphere of the receiver and 2) transferring heat energy from the concentrated solar energy to drive the endothermic chemical reaction of the reactants flowing through the reactor tubes 202, 204, 206, 208. An indirect radiation driven geometry, absorbing cavity, receiver of the solar-driven chemical reactor, an inner wall of the receiver may also be used. The inner wall and the reactor tubes 202, 204, 206, 208 may exchange energy primarily by radiation, rather than convection or conduction. This can allow for the reactor tubes 202, 204, 206, 208 to achieve a fairly uniform temperature profile even though the concentrated solar energy is merely directly impinging on the reactor tubes 202, 204, 206, 208 from one direction. The radiation heat transfer from the inner wall and the reactor tubes 202, 204, 206, 208 drives the chemical reaction.

The biomass particles may be fed to a multi-tube downdraft solar thermal receiver/reactor, in which the biomass is gasified in the presence of steam at a range of temperatures with the exit gas temperature exceeding 900° C. An alternative design may include updraft reactor or fluid bed reactor. The receiver's use of an indirect radiation, absorbing cavity receiver with multiple tubular downdraft particle reactors is new to the solar thermal processing world as well as the biomass gasification world.

Radiant heat transfer differs significantly from convective heat transfer and conductive heat transfer. In radiant heat, both reflectivity and emissivity of all bodies in the inner wall and tubes are wavelength dependent. The temperature determines the wavelength distribution of the electromagnetic radiation as limited in intensity by Planck's law of black-body radiation. For any body, the reflectivity depends on the wavelength distribution of incoming electromagnetic radiation and the emissivity depends on the wavelength distribution. Thus, whether the wavelengths of the electromagnetic radiation are coming from the Sun/solar radiation or a separate radiant heat source is a significant design consideration because the reflectivity and emissivity of walls controls its ability to radiate the heat (radiant heat transfer) to the desired reactant gas, which needs a minimum amount of heat energy to initiate and sustain the desired chemical reaction.

An insulating cavity approach is essentially a blackbody cavity. Conductive losses can be controlled by changing the thickness of the insulation, and convective losses can be controlled through aperture design, orientation, and cavity working fluid (buoyancy). The key advantage of the blackbody cavity is control of the radiative losses, which are entirely determined by the cavity temperature and the average concentration at the aperture. The cavity acts like an oven, spreading heat flux around through radiation and giving a much more even flux profile on the reactor tubes 202, 204, 206, 208 (azimuthally and axially) than the incident solar radiation has. This is a major advantage for a solar field, where the moving sun may shift the solar flux from a west to an east weighting across the aperture through the course of each day.

Figure 3:
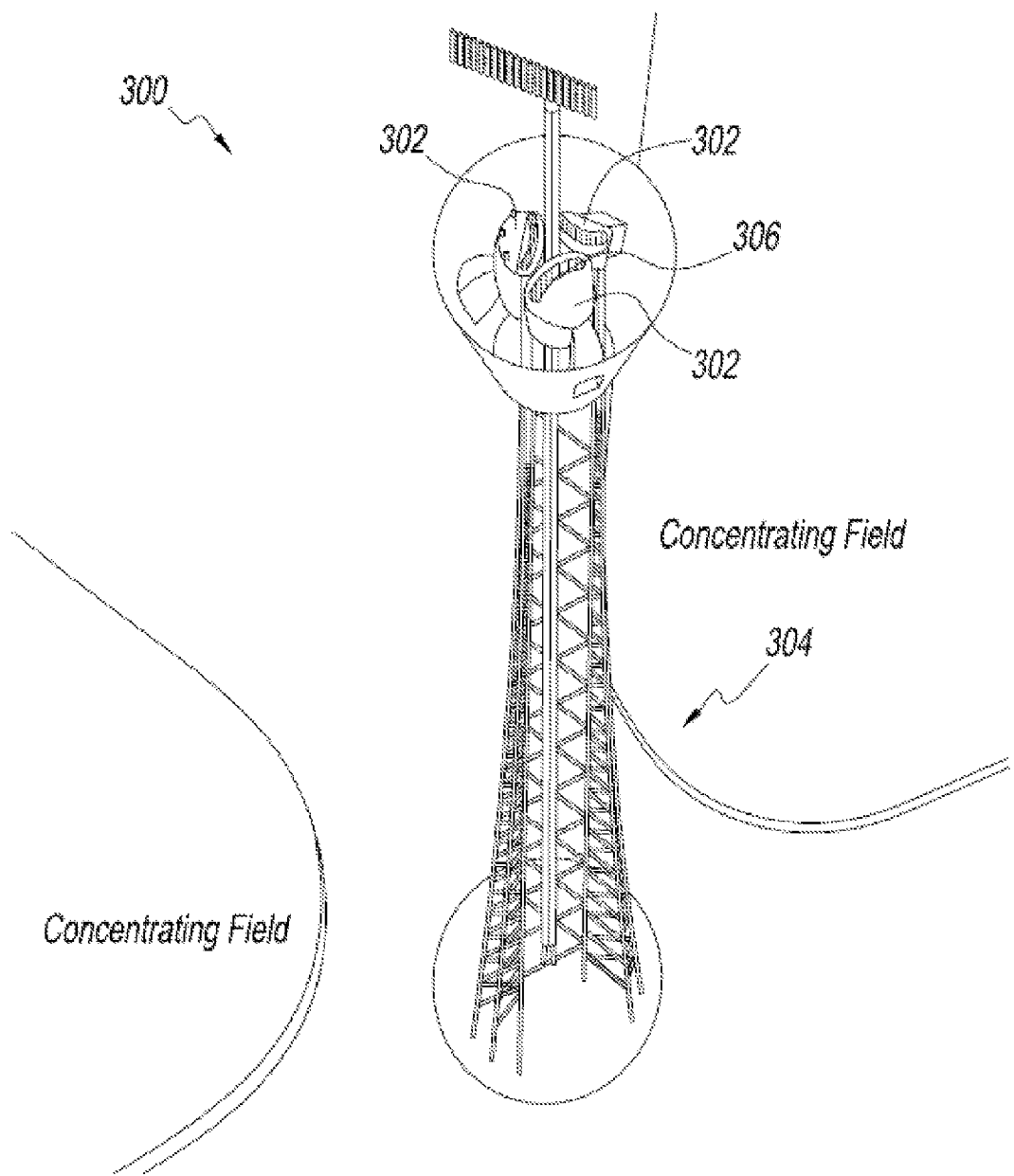
FIG. 3 illustrates a diagram of an embodiment of an example solar tower with receivers and heliostat field.

FIG. 3 illustrates a diagram of an example solar tower 300 with receivers 302 and heliostat field 304. In some embodiments solar tower 300 may be used in a solar-driven biorefinery with a biomass feed system. The feed system can be feedstock flexible.

A chemical reactor 306 receives concentrated solar thermal energy from an array of heliostats 304. The chemical reactor 306 can be, for example, a multiple reactor tube, downdraft, solar-driven, chemical reactor 306, which receives concentrated solar thermal energy from the array of heliostats 306. A solar tower 300 may form a portion of a solar-driven biorefinery that may also include a biomass feed system that has balancing of the feed lines to each of the reactor tubes in a multiple tube chemical reactor 306. For example, biomass may be fed to the solar reactor 306 in an operation including three parts: biomass transport and preparation for feeding to the solar tower reactor 300, biomass transport to the top of the, e.g., 500+ foot tower, and distribution into the specific downdraft tubes of the reactor. The distribution may be performed via multiple stages.

The solar thermal gasifier has a downdraft geometry. The tubes are oriented vertically in the solar receiver cavity, and are, for example, 3.5" in inner diameter with, for example, a 0.3125", wall thickness to withstand at least 75 psig pressure on the inside tube walls.

An absorbing solar receiver cavity exists in which the gasification reactor tubes run vertically. Solar energy enters the cavity through an aperture open to the atmosphere and impinges on the reactor tubes and the cavity walls. The walls and tubes exchange energy primarily by radiation, allowing for the tubes to achieve a fairly uniform temperature profile even though solar energy is only impinging on the tubes from one direction.

An example receiver cavity is a sectioned cylinder, with an internal diameter of 15 m. The inside walls are constructed of a thermal shock resistant refractory material. Outside of this plate layer is alumina (or similar material) fiber insulation with a thickness of 24 cm, which is contained by a structural carbon steel shell (0.090" wall thickness). There is an air gap (2") beyond this carbon steel shell, followed by a second carbon steel shell of the same thickness as before, which will further contain the conductive losses from the cavity. The top and bottom surfaces of the cavity are similarly constructed. The wall thickness of the insulation has been designed so as to limit losses to less than 5% of the energy incident on the receiver aperture.

The reactor cavity is operated at high temperature (>1200° C.) to enable the high heat transfer rates, rapid reaction kinetics, and high selectivity to syngas described above. The materials of construction for such an application must be able to mechanically and chemically withstand these temperatures.

For example, the chemical reactor can also be constructed of a transparent material, allowing radiation to pass directly through the containing reactor tube and impinge on the reactive particles. This tube could be constructed of any high temperature capable transparent material, and sapphire is a preferred material for this application. Sapphire or a Sapphire based compound has good high temperature properties, high transmission and low absorption in the visible and IR, making it well suited to this application.

In another example, the receiver 302 will ensure uniform distribution of energy across all the tubes. The tubes could all be of the same diameter and be fed by the same biomass feed rate, thereby all giving the same productivity. Similarly, the energy distribution may not be uniform across the receiver 302, yet the tubes are all to be fed with a same feed rate and give the same productivity. The way to achieve this would be to have tubes of different diameters, sized to deliver the same energy according to variable fluxes. The variability in the solar flux within the receiver 302 may also be addressed by controlling a corresponding variability in the individual feed rates through the equivalent tubes. Thus, many methods exist like the three examples given above for changing the number, size diameter and length of the tubes and biomass feed rate per tube to address different flux environments.

The indirect simple tubular reactor design has been discussed in topic a), but should be readdressed here. A simple design is not only less difficult to design, but less likely to fail during operation. The feedstock flexibility clearly gives an economic advantage over processes that are limited to one or a few available feedstocks. By heating the reactor tubes with solar energy (which re-radiate to the particles), the problem of generating heat for the reaction and designing the reactor to conduct the reaction (essentially the endothermic/exothermic balancing problem) is eliminated. The solar energy can be directed to where it is required.

A falling particle reactor is an efficient way to get thermal energy into reacting solid particulates (or gases). Heat transfer from the reactor tubes to the reacting and/or non-reacting particles can occur by conduction, convection, or radiation. Even the heated non-reacting particles can be used for many purposes discussed in this document. At moderate temperatures, convection and conduction dominate when transferring energy to a fluid, but these require large amounts of surface area to be effective. As a result, the solar flux on the surface transferring heat must be small, necessarily leading to low temperatures. To get around this problem, radiation heat transfer is required, which requires temperatures above 900 degrees C. (and preferably above 1200 degrees C.). However, if the surface area being radiated to is small, local temperatures will get high (>1500° C.) and efficiencies will be low. A dispersed particle reactor solves this problem by greatly increasing the receiving surface area (it is essentially the surface area of the particles), shifting the limitation to the radiating tube. The particles tend to average energy amongst themselves at these volumetric loadings, giving a uniform radial reaction profile. If it is the gas that is desired to be heated (for steam reforming of methane or methane cracking, for example), inert particles can be used as radiation receivers and convection can be used to drive energy from the particles to the gas. Because the surface area of the particles is so large (as compared to the tube surface area), convection heat transfer is no longer a limitation.

Additionally, the use of small particles increases the surface area for reaction. As reactions with gas phase components (e.g. steam, CO2) are surface area specific, the increased surface area greatly increases the reaction rate.

Figure 4:
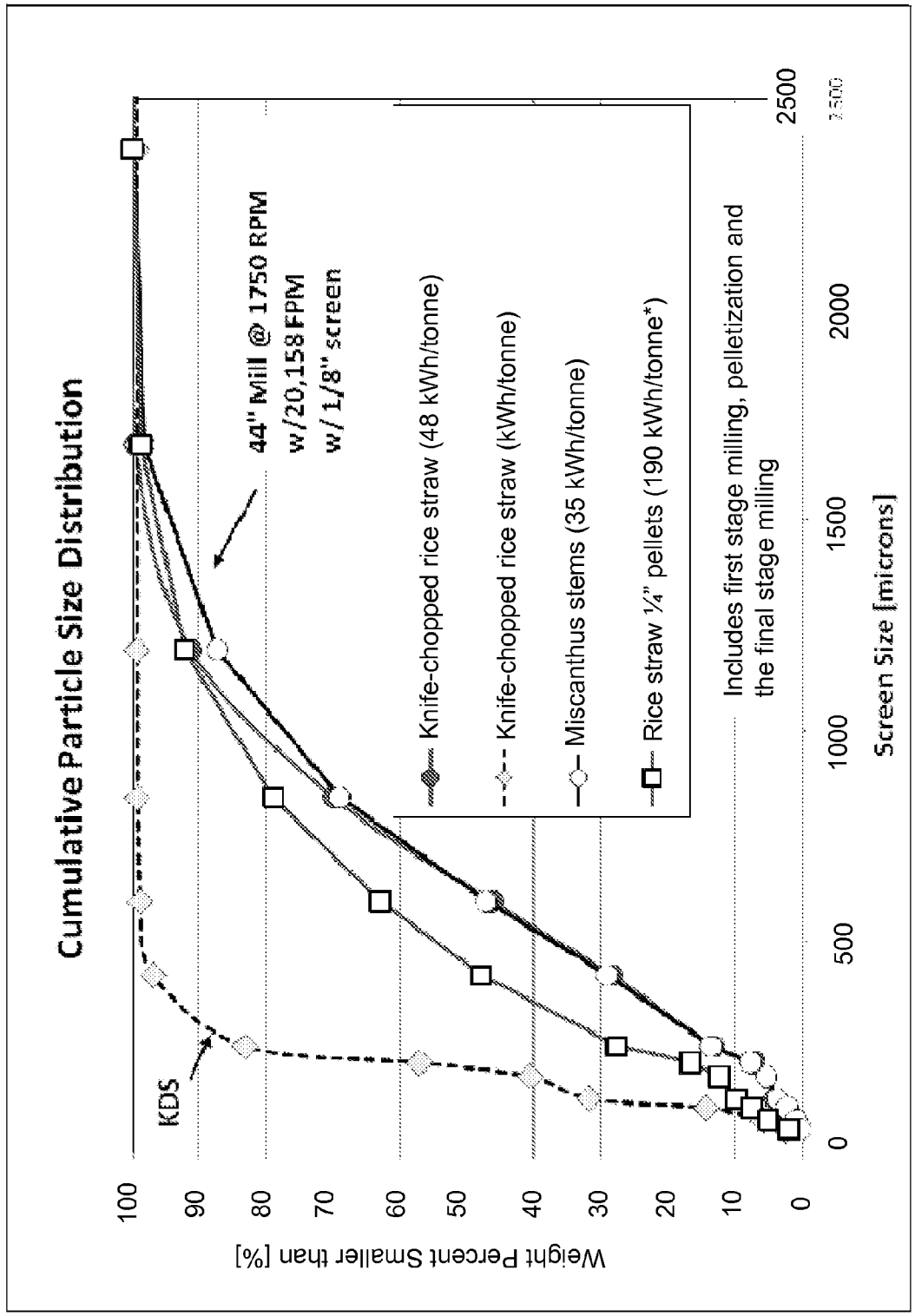
FIG. 4 illustrates a graph of an embodiment of particle size distribution of representative biomass material.

FIG. 4 illustrates a graph of cumulative particle size distribution of representative biomass material. The graph illustrates the weight percentage below Y % for a given screen size in microns. Four example materials are illustrated, knife-chopped rice straw at 48 kilowatt-hours per ton, knife-chopped rice straw with an unknown energy value per ton, miscanthus stems at 35 kilowatt-hours per ton, and rice straw at 190 kilowatt-hours per ton. The grinding system and the feed system may supply the various biomass types. The smaller the size of the particle of the various types of biomass, the less difference in the way the feed system and reactor view particles from different types of biomass. The average size of ground particles may be correlated to filter particle size used in standard filter ranges.

Figure 5:
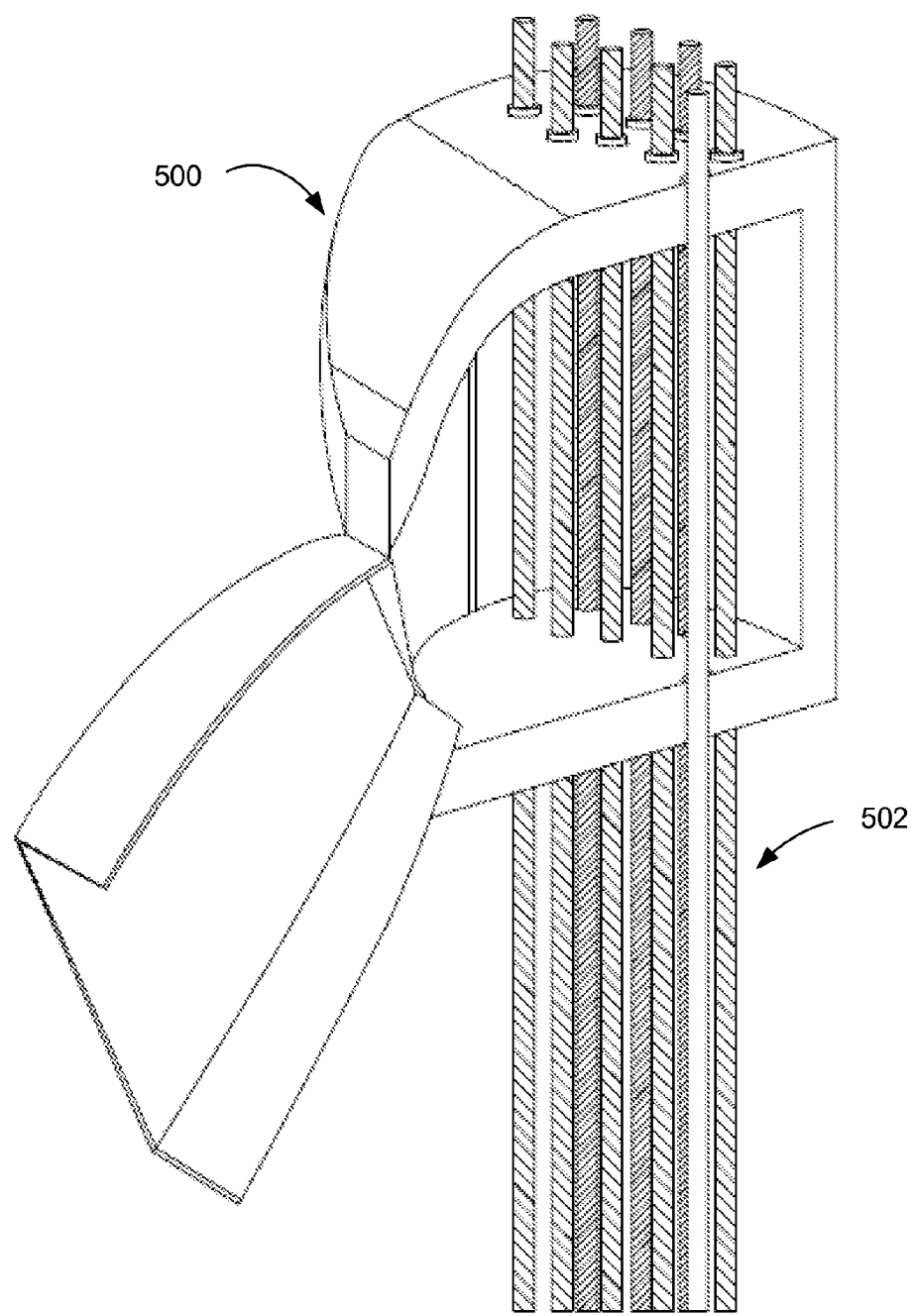
FIG. 5 illustrates a diagram of an embodiment of a solar thermal receiver with gasifier tubes.

FIG. 5 illustrates a diagram of an embodiment of a solar thermal receiver 500 with gasifier tubes 502. Solar thermal receiver 500 can form a portion of a solar-driven bio-refinery. The solar-driven bio-refinery can include a solar-driven chemical reactor, a solar thermal receiver such as receiver 500, or both as shown in FIG. 5. In some embodiments, solar thermal receiver 500 can be a multiple reaction tube downdraft solar thermal receiver as well as solar-driven chemical reactor. Additionally, the feed system may feed biomass particles into the multiple reaction tubes 502, in which the particles of biomass may be gasified in the presence of steam at a temperature exceeding 950 degrees C. from an exit of a gasification reaction zone of the reactor tubes.

In some embodiments, a solar-driven chemical plant can include a solar thermal receiver to absorb concentrated solar energy from an array of heliostats. A solar-driven chemical reactor that has multiple, for example, vertically oriented reactor tubes in a downdraft geometry, fluidized bed, or other reactor geometry. The reactor tubes may be located inside the solar thermal receiver. Additionally, in the multiple reactor tubes particles of biomass may be gasified in the presence of a carrier gas in a gasification reaction to produce hydrogen and carbon monoxide products. These products can have an exit temperature from the tubes exceeding 900 degrees C. Additionally, the multiple reactor tubes in this reactor design increase available reactor surface area for radiative exchange to the biomass particles as well as inter-tube radiation exchange. The reactor tubes can also isolate the reacting environment inside the tubes from the cavity receiver environment outside the tubes.

Some embodiments include no apertures open to the atmosphere of the Earth and only windows, e.g. a solid transparent material that allows passage of selected wavelengths of radiation but not passage of solids, liquids, or gases to pass the concentrated solar energy into the solar thermal receiver to impinge on the multiple reactor tubes and cavity walls of the receiver.

Some embodiments can include an indirect radiation driven geometry, in the form of an absorbing, integrating cavity, of the solar thermal receiver of the solar-driven chemical reactor and an inner wall of the cavity. The inner wall of the receiver cavity and the reactor tubes exchange energy primarily by radiation, not by convection or conduction, allowing for the reactor tubes to achieve a fairly uniform temperature profile even though the concentrated solar energy from the heliostats is merely directly impinging on the reactor tubes from one direction. Additionally, the radiation heat transfer from the inner wall and the reactor tubes is the primary source of energy driving the gasification reaction in which the small biomass particles act as millions of tiny absorbing surfaces for the radiant heat energy coming from the inner wall and the reactor tubes.

Some embodiments can include an on-site fuel synthesis reactor that is geographically located on the same site as the chemical reactor. The on-site fuel synthesis reactor may be integrated to receive the hydrogen and carbon monoxide products from the gasification reaction. The on-site fuel synthesis reactor has an input to receive the hydrogen and carbon monoxide products in a hydrocarbon fuel synthesis process performed in the on-site fuel synthesis reactor to create a liquid hydrocarbon fuel.

In some embodiments, the reactor uses the high surface area of the biomass particles to facilitate a rapid gasification reaction due to efficient heat and mass transfer. The gasification reaction is facilitated by the efficient heat transfer, which is a result of geometry and temperature.

The chemical plant may produce fuels, chemicals, or both. For example, the integrated chemical plant may make fine chemicals from this bio-refinery as well as the liquid hydrocarbon fuel. In some embodiments, the solar-driven chemical plant may include one or more apertures that might be part of an outer shell of the receiver. The receiver may at least partially enclose the multiple reactor tubes. Additionally, the inner wall of the receiver absorbs or highly reflects the concentrated solar energy from the array of heliostats to cause the radiant heat transfer to generally radiatively convey that radiant heat to the biomass particles in the reactor tubes of the solar-driven chemical reactor. In some embodiments, heat may transfer through the tube walls. Some receivers may have radiation from aperture and receiver walls thermalizing on the tube and then the reactor tube conducts this energy through the tube wall, which then re-radiates to the biomass particles.

In some embodiments, a material making up the inner wall or at least coating the inner wall of the receiver cavity may have mechanical and chemical properties to retain its structural strength at high temperatures (between 1100° C.-1500° C.). This material making up the inner wall of the receiver cavity has very high emissivity $\epsilon > 0.9$ or high reflectivity $\epsilon < 20\%$, as well as high heat capacity and low thermal conductivity for the receiver cavity. The material making up the reactor tubes possesses high emissivity, high thermal conductivity, moderate to high heat capacity. Additionally, the material making up the reactor tubes is also resistant to the oxidizing air environment in the cavity and the reducing environment of the biomass gasification reaction in order to allow the rapid gasification of dispersed falling biomass particulates with a resultant stable ash formation, complete amelioration of tar to less than 50 milligrams per normal cubic meter millimeter, and the production of the hydrogen and carbon monoxide products.

Some embodiments may allow for complete amelioration of tar to less than 200 milligrams per normal cubic meter millimeter and preferably less than 50 Mg/m^3, and the production of the hydrogen and carbon monoxide products. Additionally, an inner wall of the receiver cavity may be made of or coated with an absorbing solar energy material rather than the highly reflective material.

The receiver cavity is the insulating surroundings in which the reactor tubes sit. The reactor tubes are the tubes through which the biomass flow and in which the gasification reaction takes place. For the cavity walls, some embodiments may use a material that has either very high emissivity or high reflectivity, low thermal conductivity, and high heat capacity. For the reactor tubes, some embodiments may use high emissivity, high thermal conductivity, and moderate to high heat capacity materials. Generally, the reactor tubes might need to be able to handle the oxidative environment on only one side and the steam plus reducing environment on the other. Additionally, usually only the reactor tubes need to withstand pressure. The receiver wall might only be oxidation resistant and strong enough so as not to fall apart under its own weight at temperature.

In some example systems, inert solid particles may be entrained with biomass particles. One or more feed lines add inert solid particles entrained with biomass particles into the reactor tubes. The indirect radiation driven geometry of the receiver cavity may be configured as an indirect gasifier. The indirect gasifier has a primary mode of heat transfer of radiation to the biomass particles, and the other inert solid particles entrained with biomass particles. The inner wall of the cavity has a material and design that is configured to improve radiation heat transfer proportional to a fourth power of temperature of the cavity wall and concentrate radiant heat energy to extremely high fluxes of equal to or greater than 2 MW m−2 at the apertures. This flux, due to the indirect radiation driven geometry, allows the inner wall to transmit greater than 70% of aperture incident solar energy to the gasification reaction of the biomass particles and product sensible energy, where the cavity walls are at temperatures between 900° C. and 1500° C. In an embodiment, the extremely high fluxes of equal to or greater than 3 MW m−2 at the apertures. This flux, due to the indirect radiation driven geometry, allows the inner wall to transmit greater than 80% of aperture incident solar energy to the gasification reaction of the biomass particles.

In some embodiments, the solar-driven chemical plant can include one or more additional fixed radiant heat structures located within the cavity to store additional heat energy. The amount of stored heat in the mass of the walls of the receiver, tube walls and additional fixed radiant heat structures is set for a transfer of heat radiation from walls of the receiver, tube walls, as well as the one or more additional fixed radiant heat structures to the particles of the biomass in the aerosol stream to gasify and convert the biomass reactant into particles into the reaction products during periods of the day when the Sun is completely blocked by clouds.

Solar concentrating systems may become more efficient at higher concentrations. However, these efficiency differences might not be great at low temperature, because radiation, convection, and conduction losses are pretty low at low temperature. Thus, most development in concentrating solar power has been at low temperature (<400 degrees C.), mostly to generate steam to run electrical power plants. This is changing, however, as power producers look to go to higher temperatures (to get better Carnot efficiency) and as people look to do solar chemistry. Very high temperatures (above 900 degrees C.) start to allow radiation heat transfer schemes, which are very surface area efficient as radiation is driven by the difference in fourth power of temperatures.

The insulation thickness around the receiver is designed so as to limit losses through conductive heat loss to less than 5% of the energy incident at peak solar input on the receiver apertures. A radiation shield, such as a door, that is moveable across the aperture at night or other periods of extended shutdown to minimize an amount of radiation heat loss, which enables a rapid heat up to gasification temperatures when normal operations resume such as in the morning. The thick layer of insulation around a solar thermal receiver containing the chemical reactor is set to limit heat losses by conduction from a cavity of the receiver in conjunction with a moveable insulative door that covers a receiver aperture to limit heat losses by radiation, conduction, and convection from leaving the cavity during periods of non-operation, including inclement weather or nighttime, so that the temperature in the cavity is decreased by less than 400° C. in a 12 hour period when no concentrated solar energy is directed at the cavity aperture, where the insulation and door maintain heat energy to reduce both 1) the amount of time required to heat the receiver and reactor tubes following a down period and 2) the thermal shock and stresses imparted to the receiver and reactor materials of construction.

Figure 6A:
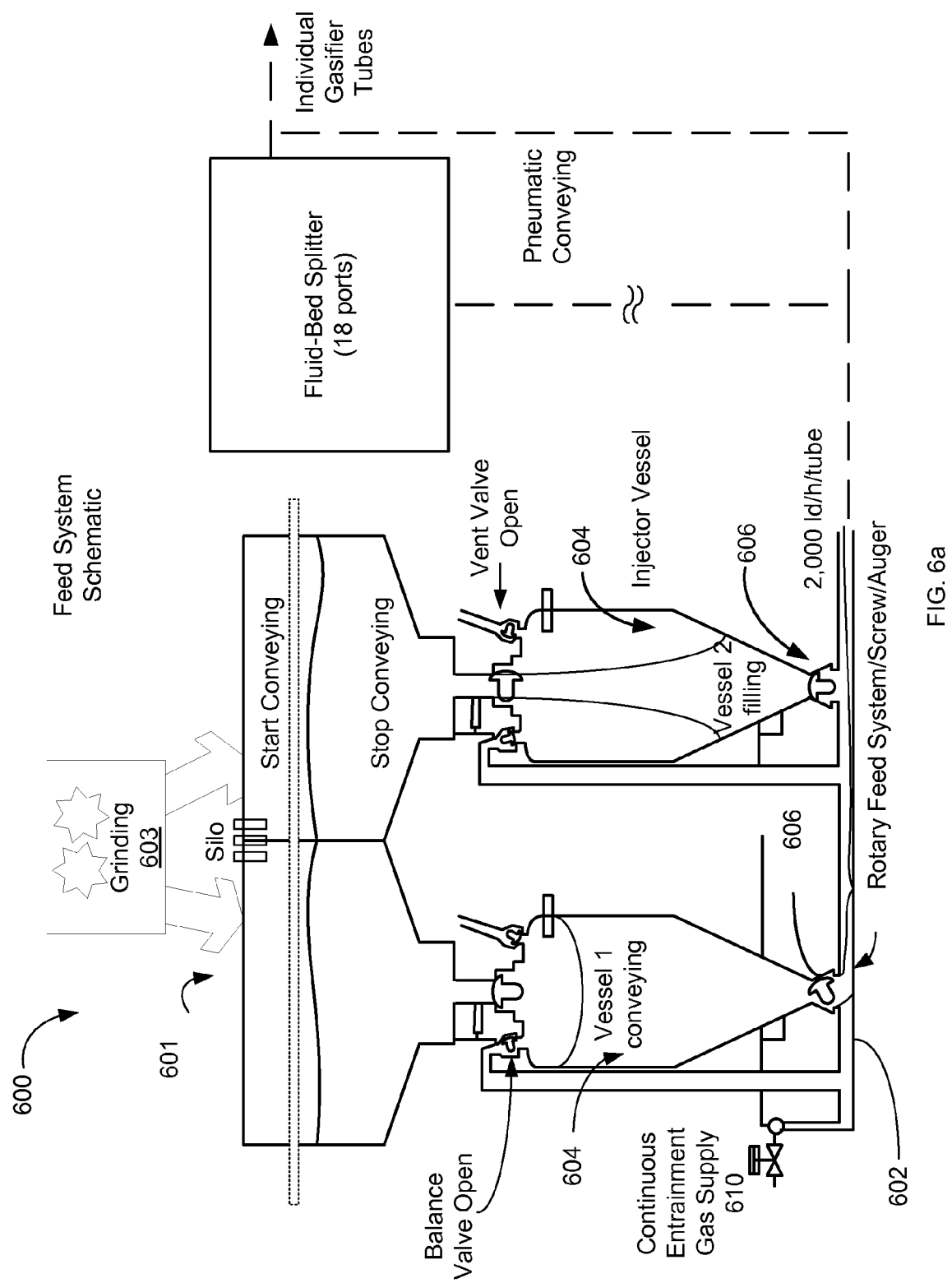
FIGS. 6a and 6b illustrate block diagrams of embodiments of the entrained-flow biomass feed system.
Figure 6B:
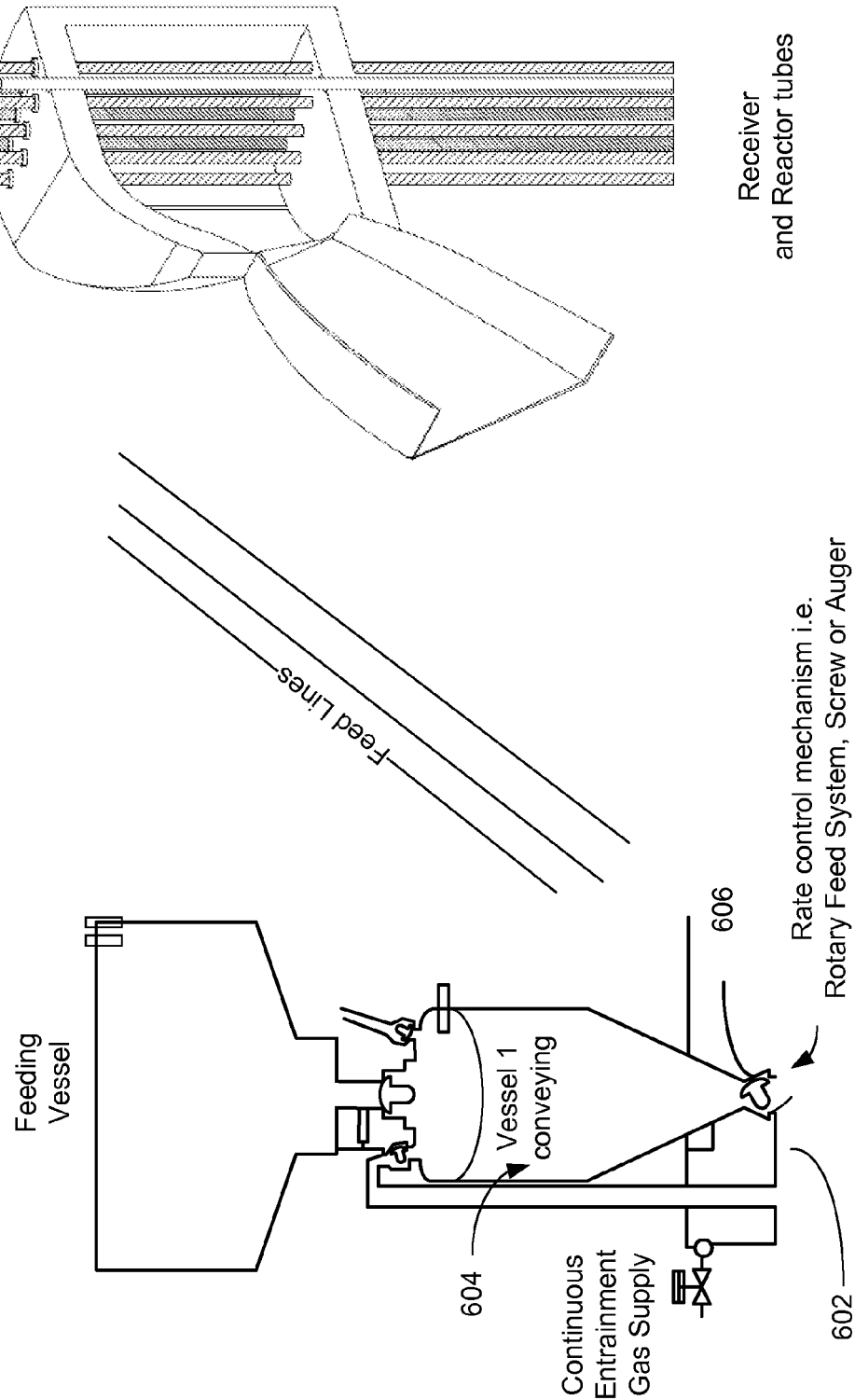

FIGS. 6a and 6b illustrate block diagrams of embodiments of the entrained-flow biomass feed system 600. Different types of feed systems may be used in conjunction with a biomass into reactor, for example, drop tube, total solid feed into the reactor, slurry fed into the reactor, a moveable bed in the reactor, or combinations of these schemes.

One or more feeding vessels in the biomass feed system supply two or more reactor tubes in the solar-driven chemical reactor. Each of the feeding vessels has one or more outlets configured to supply a consistent volumetric amount of biomass particles within 10 percent of the demand signal amount when distributing biomass particles to the two or more reactor tubes. For example, the injection rate to each injection point into carrier gas lines is within +/−10% of the desired demand signal amount.

One example solar-driven chemical plant may include the entrained-flow biomass feed system 600 that includes or otherwise cooperates with a grinding system. The grinding process 603 and feed process may be 1) processes separated in time and completed independently of the other process or 2) a continuous process of the where the grinding process 603 occurs and immediately feeds biomass into the feed system and then into the chemical reactor.

An objective of the feeding system is to feed as many reactor tubes as possible with the fewest number of feeding vessels such as lock-hopper systems.

The grinding system 603 has a mechanical cutting device used to grind bales of the biomass into primary particles, which are to be fed into the solar-driven chemical reactor, where the grinding system supplies primary particles that have an average smallest dimension size between 200 microns (um) and 2000 um, with a general range of between 500 um and 1000 um, and are loaded into a lock hopper system 604 with a standard belt conveyer and then fed across a pressure boundary into a pressurized entrainment gas for feeding into in the solar-driven chemical reactor. The feeding vessel may use an Auger/Screw feeder or an airlock-type rotational solids feeding/rate metering device.

As illustrated in FIG. 6a, the entrainment-flow biomass feed system 600 can include a pressurized lock hopper 604 that feeds the biomass to a rotating screw conveyor 602 and a metering device and then into an entrainment gas pipe at the lock hopper exit 606. A flow splitter distributes the particles of biomass into multiple entrainment gas lines to feed at least two or more of the multiple reactor tubes making up the solar driven chemical reactor. The entrainment gas for the entrainment flow biomass feed system may be a pressurized dry steam generated from waste heat recovered from either 1) the methanol/Methanol-To-Gasoline (MTG) units in the hydrocarbon fuel synthesis process or 2) the products from the gasification reaction in the solar-driven chemical reactor.

In some embodiments a solar-driven chemical plant may include a geometrical configuration of the multiple reactor tubes in the receiver relative to each other is in a cylindrical pattern or a rectangular pattern. Additionally, a pneumatic feed system configured to feed the biomass particles into the multiple reactor tubes may be used. In such a system a separate entrainment line and metering device of the pneumatic biomass feed system can be used for each of the gasifier reactor tubes in the chemical reactor. This may allow for balancing of 1) amount of particles of biomass flowing to each reactor tube to 2) temperature of that reactor tube in the multiple tube solar-driven chemical reactor.

Additionally, some systems may include a computerized control system configured to balance the amount of biomass particles flowing in each of the reactor tubes to an amount of solar energy available via, for example, a non-valve 2-phase control system. Such a system can be used to control flow in the individual reactor tubes by controlling a rotational rate of a screw/auger of a lock hopper feeding the biomass. Additionally, an amount of compression of a pinch valve configuration may be applied to a conduit such as a hose, tube, pipe, or other vessel capable of conveying materials section of each individual feed line that the biomass particles are flowing through to provide some control of flow, for example.

A feedforward and feedback control system may be configured to manage predicted changes in available solar energy as well as actual measured stochastic changes in available solar energy. For example, the control system may balance the gasification reaction between biomass feed rate and an amount energy solar energy directed at the aperture of the receiver to keep a temperature at which the reactor operates at 1) a high enough temperature for greater than 90 percent conversion of the biomass to product gases and elimination of tar products and 2) a low enough reactor tube wall temperature to not structurally weaken the walls or significantly reduce receiver efficiency.

Some embodiments may also allow for controlling the rotational rate of the screw or auger that can move set amounts of biomass along the axis of rotation of the auger. The auger may be located at the base of the lock hopper and can be controlled by a computerized control system to respond to changes in feed demand of the system. The control system hardware may be one or more of a Programmable Logic Controller, via different data communication protocols using Personal Computer, Macintosh, CNC, neural nets, analog devices, with accompanying software applications and algorithms scripted to perform various functions, or various combinations of these systems. In an embodiment, the computerized control system controls the feed rate of particles of biomass in the solar-driven chemical reactor based on an amount of solar energy available indicated by sensors including temperature sensors and/or light meters.

In some embodiments, a solar-driven chemical plant may include a dry pneumatic biomass feed system. The dry pneumatic biomass feed system may grind and pulverize biomass to a particle size controlled to an average smallest dimension size between 50 microns (um) and 2000 um, with a general range of between 200 um and 1000 um. Additionally, the dry pneumatic biomass feed system may supply a variety of biomass sources fed as particles into the solar-driven chemical reactor. (In some examples, food stock biomass might be used.) Additionally, the variety may include three or more types of biomass that can be fed, individually or in combinational mixtures, from the group consisting of rice straw, rice hulls, corn stover, switch grass, non-food wheat straw, miscanthus, orchard wastes, sorghum, forestry thinning, forestry wastes, energy crops, source separated green wastes and other similar biomass sources. The biomass may be in a raw state or partially torrified state, as long as a few parameters are controlled including particle size of the biomass and operating temperature range of the reactor tubes.

A pneumatic feed system can be configured to feed the biomass particles into the multiple reaction tubes. In these tubes a separate entrainment line and metering device of the pneumatic biomass feed system may be used for each of the gasifier reactor tubes in the chemical reactor. Additionally, each of the feed lines may control a dispersion pattern of the biomass particles into its corresponding reactor tube to maximize radiation absorption by the particles of biomass when injected into the reactor tube based on a shape and width of the outlet of the feed line pipe carrying the biomass particles to its corresponding reactor tube.

Dispersion of the particles may be controlled by the shape and width of the pipe carrying the biomass particles. Feed of biomass occurs as a dispersed particle entrained in the gas and passed through the reactor tubes. In some embodiments, dispersion may be a function of the shape and diameter of the entrained particles tube to the diameter of the dry steam tube. Additionally, if the diameter of the entrained particles tube is spread out in a cone shaped expansion of the tube a little ways before the entrained particle mix with the dry stream then a faster and more even distribution of the particles may occur in the dry stream and entrained particles in the carrier gas occurs.

A small number of materials may have adequate properties for the proposed tubes of the chemical reactor system. One such material may be silicon carbide protected graphite. The graphite may have the thermo-mechanical properties required, such as high temperature capability, excellent thermal conductivity, very good thermal shock resistance and fracture toughness, and high emissivity. A coating of silicon carbide between, for example, 0.005" and 0.020" thick may provide oxidation resistance. This coating can be placed on the tube through chemical vapor deposition or through direct siliconization of the graphite.

Figure 7:
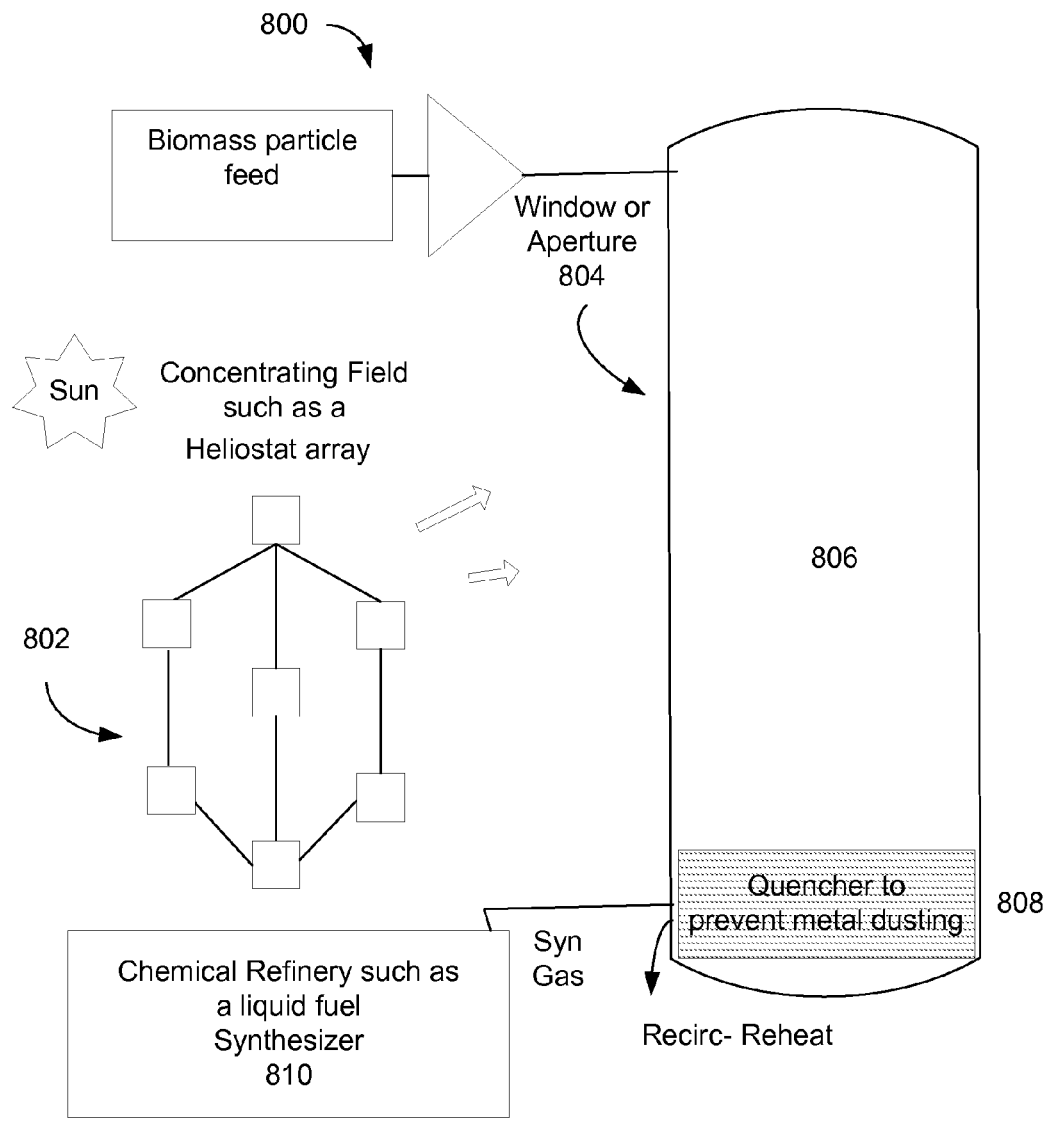
FIG. 7 illustrates a diagram of an embodiment of a solar-driven chemical plant.

FIG. 7 illustrates a diagram of a solar-driven chemical refinery 800. In such a system, solar power from a concentrating field 802 may be provided through a window or aperture 804 to a solar heated reactor chamber 806. An array of heliostats 802 can be used to focus light onto the aperture 804 of receiver around the reactor 806. A quencher 808 may be used to prevent back reaction. As illustrated, biomass particles flow into the system at 810 and syngas flows out. Additionally, a heat exchange may occur to recoup waste heat from the exiting biomass particle remnants and the syngas. Some embodiments of the solar-driven chemical plant may include insulation on an outside wall of the receiver shell to maintain heat during operations and overnight during shutdown. The insulation may be thick enough to keep conductive losses to less than 10% of the solar energy entering the aperture during operations. Examples of insulation that might be used include one or more from the group consisting of ceramic brick, ceramic blanket, and combinations of the two.

In various embodiments a small boiler or resistance heaters may be connected to the outside wall of the receiver shell of the receiver to aid in temperature control of the chemical reactor. The boiler or heater may aid in temperature control during operations, as well as during shutdown and start up operations.

In some examples a quench zone may be included immediately downstream of the exit of the chemical reactor to immediately and rapidly cool at least the hydrogen and carbon monoxide reaction products. This cooling may occur within 0.1-10 seconds of exiting the reactor, for example. The cooling may be to a temperature below a level where the product hydrogen and carbon monoxide from the gasification reaction can react to form other compounds by, for example, the water-gas shift reaction or the Boudouard reaction. Additionally, quench action in the quench zone partially occurs to prevent coalescence of ash remnants of the biomass particles coming out of the exit of the chemical reactor. Ash melts at a lower temperature then 1600 degrees C. due to a formation of a eutectic mixture with K or Na. The process quenches may partially prevent coalescence and slagging of small droplets In radiant heat, both reflectivity and emissivity of all bodies (the inner wall tubes) is wavelength dependent. The temperature determines the wavelength distribution of the electromagnetic radiation as limited in intensity by Planck's law of black-body radiation. For any body, the reflectivity depends on the wavelength distribution of incoming electromagnetic radiation and the emissivity depends on the wavelength distribution. Thus, whether the wavelengths of the electromagnetic radiation are coming from the Sun/solar radiation or a separate radiant heat source is a significant design consideration because the reflectivity and emissivity of the walls controls its ability to radiate the heat (Radiant heat transfer) to the desired reactant gas, which needs a minimum amount of heat energy to initiate and sustain the desired chemical reaction.

Some embodiments may radiantly transfer heat in order to sustain the desired chemical reaction of the reactant gas, with the electromagnetic radiation coming from the Sun/solar radiation. Additionally, the receiver reactor may have an emissivity high in both the visible and IR ranges (0.3-10 micron wavelength).

An array of heliostats 802 can be used to focus light onto a window 804 of a reactor 806. In reactor 806 biomass particles can be reduced to syngas, which in turn can be synthesized into liquid fuel in liquid fuel synthesizer 808.

Some embodiments of the solar-driven chemical plant may be configured such that, at an exit of the gasification reaction zone in the reactor tubes of the chemical reactor, the biomass gasification products from the multiple tubes may be joined into several large tubes. Additionally, water or methanol can be injected into the large tubes to rapidly cool the product gases, and water can provide steam for the water gas-shift reaction necessary to achieve a proper $H_2$ to CO ratio of syngas for fuel synthesis.

Some embodiments provide for an amount of radiation heat transfer of the cavity walls and tubes surfaces. The amount of radiation heat transfer of the cavity walls and tubes surfaces emitted per unit area in a set unit of time of the surface area is configured to increase directly proportional to the fourth power of an absolute temperature of the cavity walls and tubes surfaces, and at the exit temperature of greater than the 900 degrees C. to cause small operating temperature differences to give large changes in radiated heat fluxes from the cavity walls and tubes surfaces.

In some embodiments, the concentrated solar energy from the heliostat field is in an amount of concentration of suns provides equal to or greater than three MW per meters squared of solar energy at the apertures. This may give the receiver cavity a capacity of at least 2000 kW and generally around 60,000 kW. The multiple tube construction of the cavity may increases the surface area for radiative transfer to the biomass particles over a common reaction tube. Additionally, the shape of the reactor tubes may be substantially rectangular, which also yields a higher surface area for equivalent volume than cylindrical shaped tubes.

As the gasification is performed through indirect heating, the cavity and tube walls must be able to efficiently conduct solar energy through themselves and radiate to the reacting particles. Residence times greater than 2 seconds will be more than sufficient for the biomass to be gasified at temperatures between 500° C. and 1000° C. The key limiting factor in receiver design is heat transfer from the indirectly heated cavity wall and the reacting particulates. The net heat transfer is primarily due to radiation.

Some embodiments include an on-site fuel synthesis reactor. The on-site fuel synthesis reactor is integrated with the solar driven chemical reactor and that allows a fraction of the concentrated solar energy from the array of heliostats to be stored as an easily transportable and stable chemical energy source in the liquid hydrocarbon fuel form. The liquid hydrocarbon fuel might be at least one of jet fuel, dimethyl ether (DME), gasoline, diesel, mixed alcohol, methanol, synthetic natural gas in liquid form, and heating oil.

In some embodiments, a solar-driven chemical plant allows for feedstock flexibility in the type of biomass making up the particles of biomass. The design may also obviate any need for an exothermic/endothermic reaction balancing in the chemical reactor design because the concentrated solar energy drives the endothermic gasification reaction. Thus, at least two or more different types of biomass materials might be used in the same reactor tube geometry in some example systems. This can obviate any need for a complete reengineering when a new type of biomass feedstock is used. It will be understood that multiple feedstocks could be used simultaneously or one feedstock might be used at a time.

In some systems, feedstock might be directed by gravity and pressure through a gasification reaction zone of the reactor tubes. In such a zone temperatures of operation may be clearly delineated with the receiver cavity wall temperatures between 1100 degrees C. and 1450 degrees C. and a gas temperature from an exit of the gasification reaction zone of the reactor tubes is in excess of 900 degrees C. but not above silica melting temperatures, which is 1600 degrees C.

In some embodiments, a downdraft geometry may be used for the multiple reactor tubes. In such a geometry, the biomass particles may fall through the downdraft reactor design with an indirect path that maximizes heat transfer from reactor walls into reacting solid particulates. The dispersed particle reactor may increase the surface area for energy exchange to the gas, shifting the limitation to a maximum amount of energy that can be radiated from the tubes and cavity.

Some embodiments of a solar-driven chemical plant may include one or more feed lines to add inert heat absorbing particles. Some examples of such particles may include silica, Carbo HSP, or other proppants. These can be entrained along with the biomass particles and heat energy to drive the chemical gasification reaction of the biomass particles comes from the following three sources 1) the heat absorbing particles, 2) the reactor tubes, and 3) an inner wall of the cavity, and all that heat energy is derived from the concentrated solar energy. Additionally, an ash and particle storage mechanism may be used to accumulate the inert heat absorbing particles and ash remnants of the biomass from the gasification reaction that exit the chemical reactor. In such a mechanism, the inert heat absorbing particles and ash remnants of the biomass exit the solar reactor at the greater than 900 degrees C.

Some embodiments may also include a separator. The separator can be configured to separate the inert heat absorbing particles and ash remnants from the gas products into the ash and particle storage mechanism. The particle storage mechanism may store these particles and ash remnants to extract their heat in order to heat a working fluid that drives an electricity generation apparatus or other apparatus used in doing heat based processes. Examples of such heat extraction include preheating water, preheating gas streams, and other thermodynamic work.

Figure 8:
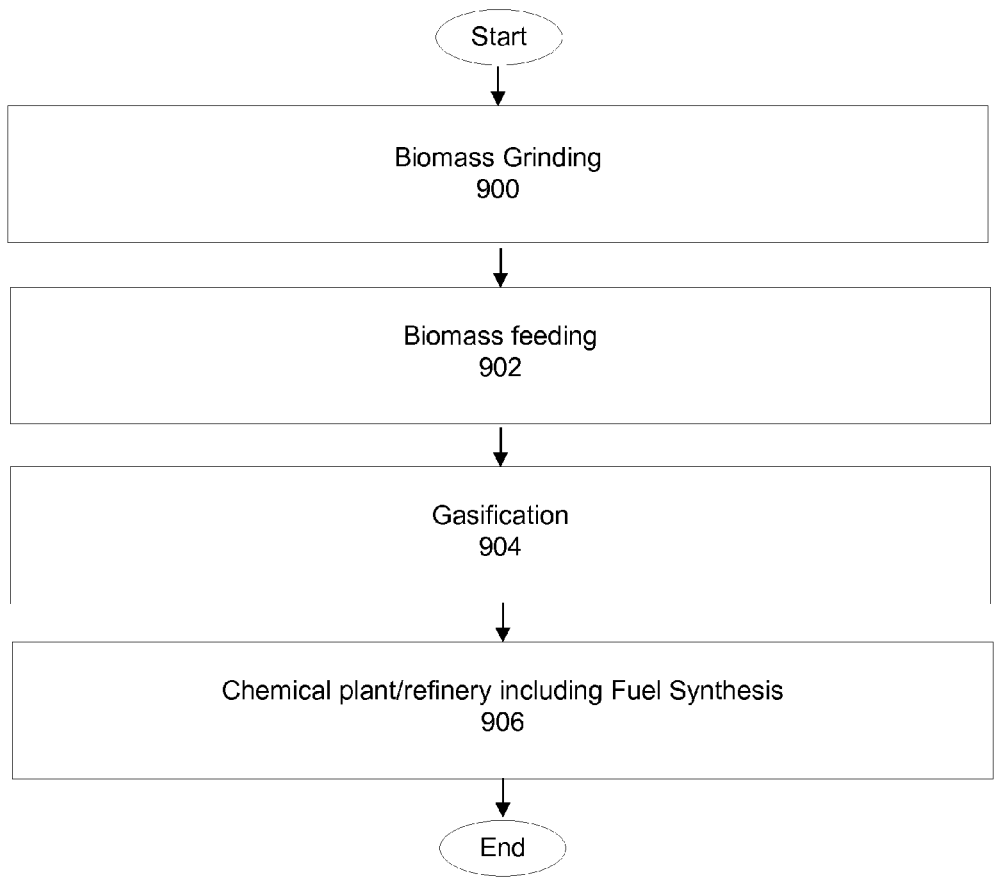
FIG. 8 illustrates a flow diagram of an embodiment of the system.

FIG. 8 illustrates a flow diagram of an embodiment of the system. In step 900, biomass grinding can occur. Equipment generally used for grinding biomass includes impact mills (e.g. hammer mills), attrition mills, and kinetic disintegration mills (e.g. flail mills). A hammer mill system can be used to grind the bales (loaded by conveyer) into primary particles, which are to be fed into the solar thermal gasifier. The re-ground particles have an average size between 500 um and 1000 um, and are loaded into the lock hopper system with a standard belt conveyer.

In step 902 biomass feeding occurs. In some embodiments, high pressure feeding may be used. High pressure feeding of solids of biomass with gasification at pressure may reduce capital cost due to the ability to use smaller compressors in some such systems. Additionally, operating cost may be reduced because energy for pressurizing carrier gas comes from the sun, as opposed to from electricity. The lock hopper system can feed the reactor processes at pressure. For example, the feeding system can entrain the biomass materials in steam at high pressure, successfully disengage the particulates in the cyclone system, and distribute flow appropriately to the reactor tubes.

In step 904 gasification occurs. For example, in some embodiments, concentrated solar thermal energy drives gasification of the particles of the biomass to generate at least hydrogen and carbon monoxide products from the gasification reaction.

In step 906 fuel synthesis occurs. An on-site fuel synthesis reactor can receive the hydrogen and carbon monoxide products from the gasification reaction and use the hydrogen and carbon monoxide products in a hydrocarbon fuel synthesis process to create a liquid hydrocarbon fuel. The fuel synthesis reactor may be geographically located on the same site as the chemical reactor and integrated into the process to utilize the hydrogen and carbon monoxide products from the gasification reaction.

In some embodiments, a solar receiver may be constructed with a multi-layered insulative outer shell. The shell can include a thin, high temperature, thermal shock resistant insulating inner layer, for example, on an internal surface of a cavity wall. This layer may generally include a refractory ceramic fiber material. Such materials can include papers, felts, blankets or boards. The inner layer may protect high density refractory brick from thermal shock that might otherwise tend to destroy the brick.

The solar receiver can also include a high temperature, high heat capacity, and low-to-moderate thermal conductivity insulating intermediate layer. This layer might generally be constructed of brick or other castable refractory materials. In some embodiments, the intermediate layer may hold a significant amount of high temperature thermal energy so that if a cloud were to pass in front of the sun, the receiver might stay hot longer. This can attenuate the loss of heat delivered to the reactor tubes during times of cloud cover. Accordingly, the biomass feed system can have more time to respond to this change before cooling down the reactor and causing poor performance or incomplete gasification.

The solar receiver can also include a low density, low thermal conductivity insulating layer that might be constructed of a single layer or multi-layers. The insulating layer that may also include air gaps. In some embodiments, the insulating layer may be constructed of blanket modules fabricated from ceramic fiber, mineral wool, or fiberglass. A, for example, low density outer layer of insulation can reduce heat losses from the receiver.

In some embodiments, a solar receiver can include an inner surface of an inner layer that is made of a high emissivity refractory material. For example, the material might be imbedded with an additive such as metal oxides, carbides, or nitrides in either particulate or fiber form (e.g. SiC fibers). These materials might be integrated into the original manufacturing of these layers or applied by a spray process like guniting. High emissivity refractory material may improve the ability of the surface layer to absorb and re-emit radiation energy to the reactor tubes instead of just reflecting the instantaneously available insolation, which may be subject to variability from clouds, etc.

In various embodiments, a receiver's outer shell may be constructed of layered high temperature refractory insulation. An outer layer, e.g., closest to external steel enclosure, may be constructed of low density low thermal conductivity refractory fiber module insulation. A low density outer layer of insulation may reduce heat losses from, for example, the receiver to a minimum. An intermediate layer may be constructed of high density refractory brick. The intermediate layer may hold a significant amount of high temperature thermal energy. Accordingly, if a cloud were to pass in front of the sun, the receiver may continue to stay hot longer. This can attenuate losses of heat delivered to the reactor tubes. Accordingly, biomass feed system may have more time to respond to this change, e.g., cloud cover, before cooling down the reactor and causing poor performance or incomplete gasification.

In various embodiments, an inner layer, e.g., internal surface of cavity wall, may also be constructed of low density refractory fiber module insulation. Generally, an inner layer may protect high density refractory brick from thermal shock that might otherwise tend to destroy the brick.

Additionally, the inner layer may be made of a high emissivity refractory material. Generally, such a material may be a high temperature refractory insulation materials. In some embodiments a material may be imbedded with an additive such as metal oxides, carbides, or nitrides in either particulate or fiber form to form a high temperature refractory insulation material.

The methods and apparatuses of the invention in some cases may be implemented using computer software. If written in a programming language conforming to a recognized standard, sequences of instructions designed to implement the methods can be compiled for execution on a variety of hardware platforms and for interface to a variety of operating systems. It will be appreciated that a variety of programming languages may be used to implement the teachings of the invention as described herein. Furthermore, it is common in the art to speak of software, in one form or another (e.g., program, procedure, application, driver, etc.), as taking an action or causing a result. Such expressions are merely a shorthand way of saying that execution of the software by a computer causes the processor of the computer to perform an action or produce a result.

A machine-readable medium is understood to include any mechanism for storing or transmitting information in a form readable by a machine (e.g., a computer). For example, a machine-readable medium includes read only memory (ROM); random access memory (RAM); magnetic disk storage media; optical storage media; flash memory devices, etc.

While some specific embodiments of the invention have been shown the invention is not to be limited to these embodiments. The invention is to be understood as not limited by the specific embodiments described herein, but only by scope of the appended claims.

We claim:

1. An apparatus, comprising:
a thermal receiver having walls that form a cavity space inside the thermal receiver;
a chemical reactor that has multiple reactor tubes located inside the cavity space of the thermal receiver, where in the multiple reactor tubes a chemical reaction driven by radiant heat is configured to occur, wherein the chemical reaction includes one or more of biomass gasification, steam methane reforming, methane cracking, steam methane cracking to produce ethylene, metals refining, and CO2 or H2O splitting to be conducted in this chemical reactor using the radiant heat;
a source of inert particles that are inert to the chemical reaction that includes one or more of biomass gasification, steam methane reforming, methane cracking, steam methane cracking to produce ethylene, metals refining, and CO2 or H2O splitting to be conducted in this chemical reactor using the radiant heat at the temperature of 900 degrees C. or more, where the source of inert particles couples to the one or more feed lines to add the inert particles to the chemical reactor;
one or more feed lines coupled to the chemical reactor to add inert particles for radiation absorption and re-radiate radiation with the chemical reactants for the chemical reaction;
an indirect radiation driven geometry in the form of the cavity wall of the thermal receiver integrates and locates the chemical reactor inside the receiver, where the inner wall of the receiver cavity and the multiple reactor tubes exchange energy primarily by radiation creating an oven effect, allowing for the multiple reactor tubes to achieve a fairly uniform temperature profile along a length of the reactor tubes, where the multiple reactor tube design increases a surface area to radiate the radiation to the inert particles and other chemical reactants in the chemical reaction;
a heat source to heat the chemical reactor to 900 degrees C. or more and to cause the indirect radiation driven geometry in the form of the cavity wall of the thermal receiver and multiple reactor tubes to supply the radiant heat to drive the chemical reaction with the fairly uniform temperature profile along the length of the reactor tubes; and
an exit area of a gasification zone in the multiple reactor tubes, wherein reaction products have a temperature from the exit area of the gasification zone that equals or exceeds 900 degrees C.

2. The chemical plant of claim 1, further comprising:
where the thermal receiver has cavity walls;
wherein the chemical reaction is the biomass gasification, where particles of biomass are gasified in the presence of a carrier gas in an endothermic gasification reaction inside the multiple reactor tubes to produce hydrogen and carbon monoxide products;

where the multiple reactor tubes in this driven chemical reactor design increase available reactor surface area for radiative exchange to the biomass particles and inert particles, as well as inter-tube radiation exchange resulting in even distribution of heat energy;

wherein the reactor tubes serve the dual functions of 1) segregating the biomass gasification reaction environment from the atmosphere in the thermal receiver and 2) transferring energy by radiation absorption and heat radiation, convection, and conduction to the reacting particles of biomass to drive the endothermic gasification reaction of the particles of biomass flowing through the reactor tubes, and wherein high heat transfer rates of the reactor tubes and cavity walls allow the particles of biomass to achieve a high enough temperature necessary for substantial tar destruction and gasification of greater than 90 percent of the biomass particles into reaction products including the hydrogen and carbon monoxide gas in a short residence time; and wherein the inner wall of the receiver absorbs or highly reflects the energy from the heat source to cause energy transport by thermal radiation or reflection to generally convey that heat to the biomass particles via the walls of the chemical reactors.

3. The chemical plant of claim 2, further comprising:

a material making up the inner wall of the receiver cavity has mechanical and chemical properties to retain its structural strength at high temperatures between 1100-1500° C., have very high emissivity of $\epsilon > 0.8$ or high reflectivity of $\epsilon < 0.2$, as well as high heat capacity (>200 J/kg-K) and low thermal conductivity (<1 W/m-K) for the receiver cavity; and a material making up the reactor tubes possesses high emissivity ($\epsilon > 0.8$), high thermal conductivity (>1 W/m-K), moderate to high heat capacity (>150 J/kg-K), wherein the one or more apertures are part of an outer shell of the receiver and the material making up the reactor tubes is also resistant to the oxidizing air environment in the cavity and the reducing environment of the biomass gasification reaction.

4. The chemical plant of claim 2, further comprising:

where the added inert particles are inert solid particles entrained with biomass particles or reactant gases into the reactor tubes, wherein the indirect radiation driven geometry of the thermal receiver is configured as an indirect gasifier with a primary mode of heat transfer of radiation to the biomass particles and the inert solid particles entrained with biomass particles, wherein the inner wall of the cavity acts as a radiation distributor by either absorbing solar radiation an re-radiating to the reactor tubes or reflecting the incident radiation to the tubes, where the radiation is absorbed by the reactor tubes, and the heat is transferred, by conduction to the inner wall of the reactor tubes, where it radiates to the reacting particles at temperatures between 900° C. and 1400° C., wherein the inner wall of the receiver cavity is made of the absorbing solar energy material rather than the highly reflective material, and wherein the rapid gasification of dispersed falling biomass particulates with a resultant stable ash formation, complete amelioration of tar to less than 500 milligrams per normal cubic meter, and the production of the hydrogen and carbon monoxide products occurs.

5. The chemical plant of claim 2, further comprising:

wherein a shape of the reactor tubes is substantially cylindrical shaped tubes.

6. The chemical plant of claim 2, further comprising:

wherein the multiple tube construction of the chemical reactor increases the surface area for radiative transfer to the biomass particles over a simple single reaction tube, and a shape of the reactor tubes is substantially rectangular, which also yields a higher surface area for equivalent volume than cylindrical shaped tubes.

7. The driven chemical plant of claim 2, further comprising:

a downdraft geometry to the multiple reactor tubes in which the biomass particles fall through the downdraft reactor design, where the downdraft permits disengagement of volatile alkali and tar components prior to cooling and remediation on the non-volatile ash, wherein the reactor tube walls are at a temperature of greater than the 900 degrees C. with high heat transfer rates that allow the biomass particles to achieve the high temperatures necessary for tar destruction and complete gasification in the very short residence times of at least 0.01 seconds.

8. The driven chemical plant of claim 2, further comprising:

two or more feed lines to the multiple reactor tubes, where each feed line supplies a reactor tube, and controls a dispersion pattern of the biomass particles into its corresponding reactor tube to maximize radiation absorption by the particles when injected into the reactor tube based on a shape and width of the outlet of the feed line pipe carrying the biomass particles to its corresponding reactor tube; and the two or more feed lines supply the particles of biomass having an average smallest dimension size between 50 microns (um) and 2000 um, and the small particle size and large surface area of the dispersed particles ensures there is a low temperature gradient within the particles, high mass transfer between the particles surface with water vapor in the entrainment gas, and efficient heat transfer to the reactant gases from the particles, facilitating gasification of biomass particles in the short residence times of at least 0.01 seconds.

9. The chemical plant of claim 2, further comprising:

an insulation layer around the cavity of the solar thermal receiver; wherein the receiver is configured with only one or more apertures and no windows, where the multiple reactor tubes are located in the center of the cavity;

a thickness of the insulation layer is set to control conductive heat losses from the cavity, and the heliostats are aligned with the one or more apertures in the cavity and the apertures are sized to have a high average concentration of solar energy greater than 1000 suns at the one or more apertures, and where a shape of the cavity is designed so an average temperature in the cavity and the average concentration of solar energy at the one or more apertures control radiative losses from the cavity;

a design and orientation of the aperture, and cavity working fluid (buoyancy) are set to control convective losses, wherein the inner cavity wall at least partially encloses the multiple reactor tubes to act like an oven, spreading heat flux around through radiation and giving a much more even flux profile on the reactor tubes, both azimuthally and axially, than the incident solar radiation by itself has, wherein an averaging effect on the heat flux radiated from the absorbing cavity walls and multiple tubes occurs within the cavity; and a heliostat field that focuses the moving Sun to shift the average concentrated solar energy weighting from West to East across the aperture and impinging on the axis of the reactor tubes themselves through the course of each day, and wherein 1) the oven effect of the cavity along with 2) the particles of biomass, which tend to average energy amongst themselves at their design volumetric loadings, combine to give the fairly uniform temperature profile and subsequent fairly uniform radial reaction profile of the biomass particles.

10. The chemical plant of claim 2, further comprising:
a length and diameter dimensions of the gasification reaction zone of each of the reactor tubes, along with an arrangement and an amount of the tubes are matched to the radiant heat from the heat source to allow high heat transfer and to give the fast reaction time of at least 0.01 seconds at the gasification temperatures,
wherein the inside walls of the receiver cavity are constructed of a high temperature-resistant refractory material including one or more of SiC, alumina plate, alumina/SiO2 fiber, and
wherein a first of the multiple tubes has a different diameter than a second of the multiple tubes, and where a shape of each tube is a cylindrical shaped pipe.

11. The chemical plant of claim 2, further comprising:
where the gasification reaction zone in the multiple tubes has an inner atmosphere of the tubes, which is sealed from the environment present in the cavity; and
a substantial axial length of the reactor tube, where the biomass particles are passed through the reaction zone of the reactor tube along a predetermined path which is substantially coincident with the reactor tube axis, and the biomass particle reactants are confined entirely within the reactor tube, wherein an arrangement of the cavity causes high flux (100-300 kW/m$^2$) radiant energy from the walls and tubes to be directed through the reactor tubes to coincide with the reaction zone of each reactor tube.

12. The chemical plant of claim 2, further comprising:
a thick layer of insulation around a solar thermal receiver containing the chemical reactor is set to limit heat losses by conduction from a cavity of the receiver in conjunction with a moveable insulative door that covers a receiver aperture to limit heat losses by radiation, conduction, and convection from leaving the cavity during periods of non-operation, including inclement weather or nighttime, so that the temperature in the cavity is decreased by less than 400° C. in a 12 hour period when no concentrated solar energy is directed at the cavity aperture, where the insulation and door maintain heat energy to reduce both 1) the amount of time required to heat the receiver and reactor tubes following a down period and 2) the thermal shock and stresses imparted to the receiver and reactor materials of construction.

13. The chemical plant of claim 2, further comprising:
a first on-site fuel synthesis reactor that is geographically located on the same site as the chemical reactor and integrated to receive the hydrogen and carbon monoxide products from the gasification reaction, wherein the on-site fuel synthesis reactor has an input to receive the hydrogen and carbon monoxide products in a hydrocarbon fuel synthesis process performed in the on-site fuel synthesis reactor to create methanol, and a second fuel synthesis reactor connected downstream of the first fuel synthesis reactor and configured to produce liquid hydrocarbon fuels or chemicals, wherein the liquid hydrocarbon produced from the on-site fuel synthesis reactor is one or more of jet fuel, dimethyl ether (DME), gasoline, diesel, mixed alcohol, methanol, synthetic natural gas in liquid form, hydrocarbon chemicals, and heating oil.

14. The chemical plant of claim 2, where a material and an indirect, heated gasification design of the multiple reactor tubes allows for feedstock flexibility in the type of biomass making up the particles of biomass, and obviates any need for an exothermic/endothermic reaction balancing in the chemical reactor design because the energy from a heat source drives the endothermic gasification reaction and a radiation-based heat transfer balancing makes the endothermic reaction gasification quite forgiving in terms of internal reaction balance, and thus, at least two or more different types of biomass materials can be used in the same multiple reactor tube geometry of the chemical reactor, obviating any need for a complete reengineering when a new type of biomass feedstock is used.

15. The chemical plant of claim 1,
wherein the inert heat absorbing particles, including silica, Carbo HSP, or other proppants, entrained along with the biomass particles, and where heat energy to drive the gasification reaction of the biomass particles or partially reacted gas comes from the following three sources 1) the heat absorbing particles, 2) the reactor tubes, and 3) an inner wall of the cavity;
an ash and particle storage mechanism configured to accumulate the inert heat absorbing particles and ash remnants of the biomass from the gasification reaction that exit the chemical reactor; and
a separator configured to separate the inert heat absorbing particles and ash remnants from the gas products into the ash and particle storage mechanism.

16. The chemical plant of claim 2, further comprising:
one or more windows covering the apertures in a shell of the receiver, wherein a first window is constructed of material at least partially transparent to visible radiation but reflecting to infrared radiation, which allows the re-radiation from the hot cavity to be trapped and redirected to the reactor tubes, improving overall efficiency, where the first window is constructed of one or more of the following materials quartz, sapphire, tiled sheets of sapphire, and coated with any number of anti-reflective and reflective coatings to achieve the desired suite of reflective and transmissive properties, and a protective gas purge may be used, and
wherein a chamber of the solar thermal receiver contains additional radiant heat masses to the reactor tubes, which have high temperature (>1400° C.) capable storage material that absorb the concentrated solar energy, where the radiant heat masses are used to keep the reactor tubes hot during long periods of off sun, during cyclic up and down times in the plant, as well as keep temperature in the reactor less transient during normal operation when instantaneous solar flux can vary.

17. The chemical plant of claim 2, further comprising:
a hood made of metal or ceramic that overhangs an aperture of the receiver cavity to disrupt convective heat transport between the receiver and the outer atmosphere;
a thin mesh made of transparent high temperature (>1300° C.) ceramic or high heat resistance steel material that covers a first aperture in the receiver cavity in order to keep undesirable objects from entering the cavity from the environment; and
wherein the solar-thermal receiver has one or more apertures and no windows.

* * * * *